US009952201B2

(12) United States Patent
Baudouin et al.

(10) Patent No.: US 9,952,201 B2
(45) Date of Patent: Apr. 24, 2018

(54) METHOD FOR EVALUATING THE HARMFUL EFFECTS OF UV ON CHILDREN'S SKIN

(71) Applicant: LABORATOIRES EXPANSCIENCE, Courbevoie (FR)

(72) Inventors: Caroline Baudouin, Rambouillet (FR); Stephanie Bredif, Croisilles (FR); Philippe Msika, Versailles (FR)

(73) Assignee: LABORATORIES EXPANSCIENCE, Courbevoie (FR)

(*) Notice: Subject to any disclaimer, the term of this patent is extended or adjusted under 35 U.S.C. 154(b) by 0 days.

(21) Appl. No.: 15/023,882

(22) PCT Filed: Sep. 24, 2014

(86) PCT No.: PCT/EP2014/070411
§ 371 (c)(1),
(2) Date: Mar. 22, 2016

(87) PCT Pub. No.: WO2015/044230
PCT Pub. Date: Apr. 2, 2015

(65) Prior Publication Data
US 2016/0245795 A1   Aug. 25, 2016

(30) Foreign Application Priority Data
Sep. 24, 2013 (FR) .................................... 13 59189

(51) Int. Cl.
G01N 33/53   (2006.01)
G01N 33/50   (2006.01)
G01N 33/68   (2006.01)

(52) U.S. Cl.
CPC ..... *G01N 33/5023* (2013.01); *G01N 33/5044* (2013.01); *G01N 33/6881* (2013.01); *G01N 2333/4721* (2013.01); *G01N 2333/545* (2013.01); *G01N 2333/5421* (2013.01); *G01N 2333/96486* (2013.01)

(58) Field of Classification Search
CPC ........... G01N 33/5023; G01N 33/5044; G01N 33/6881
See application file for complete search history.

(56) References Cited

U.S. PATENT DOCUMENTS

| 4,849,077 A | 7/1989 | Rosenthal et al. |
| 4,882,127 A | 11/1989 | Rosenthal et al. |
| 6,723,513 B2 | 4/2004 | Lexow |
| 7,556,922 B2 | 7/2009 | Block et al. |
| 2006/0275782 A1 | 12/2006 | Gunderson et al. |
| 2007/0148771 A1 | 6/2007 | Chopart et al. |
| 2008/0020392 A1 | 1/2008 | Block et al. |
| 2009/0181385 A1 | 7/2009 | McKernan et al. |
| 2009/0181860 A1 | 7/2009 | McKernan et al. |
| 2009/0186349 A1 | 7/2009 | Gunderson et al. |
| 2010/0099576 A1 | 4/2010 | Comer et al. |

FOREIGN PATENT DOCUMENTS

| EP | 0 296 78 A1 | 6/1981 |
| EP | 0 285 471 A1 | 10/1988 |
| EP | 0 789 074 A1 | 8/1997 |
| EP | 1 141 399 B1 | 10/2001 |
| EP | 1 451 302 B1 | 9/2004 |
| EP | 1 878 790 A1 | 1/2008 |
| EP | 1 974 718 A1 | 10/2008 |
| FR | 955 344 | 1/1950 |
| FR | 958 525 | 3/1950 |
| FR | 958 529 | 3/1950 |
| FR | 1 061 047 | 4/1954 |
| FR | 1 061 051 | 4/1954 |
| FR | 1 061 055 | 4/1954 |
| FR | 1 262 234 | 4/1961 |
| FR | 1 351 136 | 12/1963 |
| FR | 2 822 821 B1 | 10/2002 |
| FR | 2 857-596 B1 | 1/2005 |
| WO | WO-98/47479 | 10/1998 |
| WO | WO-00/62789 A1 | 10/2000 |
| WO | WO-01/21150 A1 | 3/2001 |
| WO | WO-01/21605 A2 | 3/2001 |
| WO | WO-01/51596 A2 | 7/2001 |
| WO | WO-02/070729 A2 | 9/2002 |
| WO | WO-03/066896 A2 | 8/2003 |
| WO | WO-2004/012496 A2 | 2/2004 |
| WO | WO-2004/012752 A2 | 2/2004 |
| WO | WO-2004/016106 A1 | 2/2004 |
| WO | WO-2004/050052 A1 | 6/2004 |
| WO | WO-2004/050079 A1 | 6/2004 |
| WO | WO-2004/112741 A1 | 12/2004 |
| WO | WO-2004/112742 A2 | 12/2004 |
| WO | WO-2005/102259 A1 | 11/2005 |
| WO | WO-2005/105123 A1 | 11/2005 |
| WO | WO-2006/063864 A2 | 6/2006 |
| WO | WO-2006/063865 A2 | 6/2006 |
| WO | WO-2006/084132 A2 | 8/2006 |
| WO | WO-2007/057439 A1 | 5/2007 |
| WO | WO-2007/064305 A1 | 6/2007 |
| WO | WO-2007/111924 A2 | 10/2007 |
| WO | WO-2008/009709 A1 | 1/2008 |
| WO | WO-2008/080974 A1 | 7/2008 |

OTHER PUBLICATIONS

Auxenfans et al., "Adipose-derived stem cells (ASCs) as a source of endothelial cells in the reconstruction of endothelialized skin equivalents," Journal of Tissue Engineering and Regenerative Medicine, vol. 6, 2012, pp. 512-518.

(Continued)

*Primary Examiner* — Prema Mertz
(74) *Attorney, Agent, or Firm* — Potomac Law Group, PLLC

(57) ABSTRACT

The invention relates to in vitro methods for testing formulations or active ingredients for preventing the harmful effects of UV on children's skin, in particular children aged three or less. The inventors have developed methods for evaluating the in vitro efficacy of formulations in preventing the harmful effects of UV on the skin of children aged three or less, using a skin model specifically capable of reproducing the characteristics of the skin of children of this age.

11 Claims, 6 Drawing Sheets

(56) References Cited

OTHER PUBLICATIONS

Figure 1:
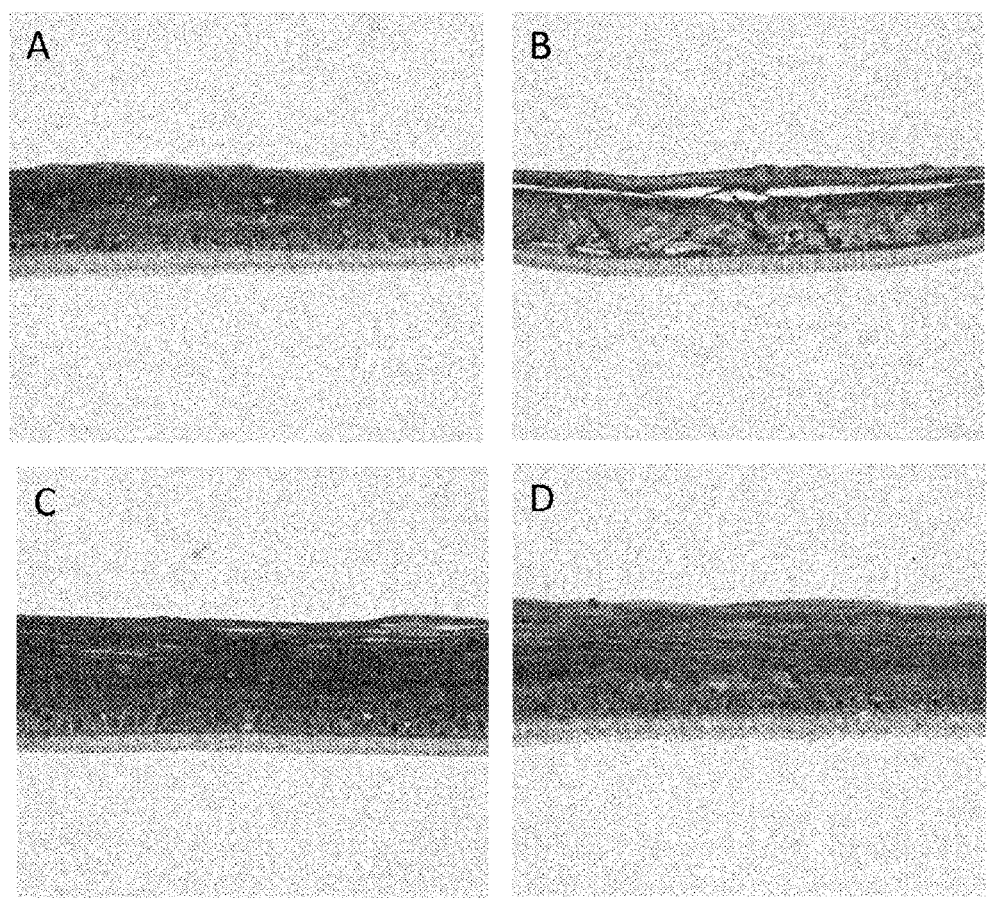

Auxenfans et al., "Evolution of three dimensional skin equivalent models reconstructed in vitro by tissue engineering," Eur J Dermatol, vol. 19, No. 2, 2009, pp. 107-113.
Baudouin et al., "Molecular biomarkers analysis to characterize epidermis of infants," Journal of investigative dermatology, May 2013, p. S106, retrieved online at: http://www.nature.com/jid/journal/v133/n1s/pdf/jid201399a.pdf.
Bechetoille et al., "Effects of Solar Ultraviolet Radiation on Engineered Human Skin Equivalent Containing Both Langerhans Cells and Dermal Dendritic Cells," Tissue Engineering, vol. 13, No. 11, 2007, pp. 2667-2679.
Black et al., "Optimization and Characterization of an Engineered Human Skin Equivalent," Tissue Engineering, vol. 11, No. 5/6, 2005, pp. 723-733.
Costin et al., "Vaginal Irritation Models: The Current Status of Available Alternative and In Vitro Tests" ATLA, vol. 39, 2011, pp. 317-337.
Diffey et al., "In vitro assessment of the broad-spectrum ultraviolet protection of sunscreen products," J Am Acad Dermatol, vol. 43, No. 6, 2000, pp. 1024-1035.
Dominik Peus et al., "Vitamin E analog modulates UVB-induced signaling pathway activation and enhances cell survival", Free Radical Biology & Medicine, vol. 30, No. 4, Feb. 2001, pp. 425-432.
Dongari-Bagtzoglou et al., "Development of a highly reproducible three-dimensional organotypic model of the oral mucosa," vol. 1, No. 4, 2006, pp. 2012-2018.
Enk et al., "The UVB-induced gene expression profile of human epidermis in vivo is different from that of cultured keratinocytes," Oncogene, vol. 25, 2006, pp. 2601-2614.
Fuller et al., "The challenges of sequencing by synthesis," Nature Biotechnology, vol. 27, No. 11, Nov. 2009, pp. 1013-1023.
Haes et al., "Two 14-epi analogues of 1,25-dihydroxyvitamin D3 protect human keratinocytes against the effects of UVB," Arch Dematol Res, vol. 295, 2004, pp. 527-534.
Horiguchi et al., "Ultrastructural and immunohistochemical characterization of basal cells in three-dimensional culture models of the skin," Arch Dermatol Res, vol. 286, 1994, pp. 53-61.
International Search Report issued in application No. PCT/EP2014/070411 dated Nov. 7, 2014.
Kinikoglu et al., "Reconstruction of a full-thickness collagen-based human oral mucosal equivalent," Biomaterials, vol. 30, 2009, pp. 6418-6425.
Kinikoglu et al., "The influence of elastin-like recombinant polymer on the self-renewing potential of a 3D tissue equivalent derived from human lamina propria fibroblasts and oral epithelial cells," Biomaterials, vol. 32, 2011, pp. 5756-5764.
Leclere-Bienfait et al., "Avocado perseose, a biomimetic active ingredient for the protection and accompaniment of infants' skin", Journal of Investigative Dermatology, May 1, 2013, p. S106, retrieved online at: http://www.nature.com/jid/journal/v133/n1s/pdf/jid201399a.pdf.

Lee et al., "Analysis of genes responding to ultraviolet B irradiation of HaCaT keratinocytes using a cDNA microarray," British Journal of Dermatology, vol. 152, No. 1, Jan. 2005, pp. 52-59.
Lee et al., "Chronic ultraviolet radiation modulates epidermal differentiation as it up-regulates transglutaminase 1 and its substrates", Photodermatology, Photoimmunology & Photomedicine, vol. 21, No. 1, Feb. 2005, pp. 45-52.
Lequeux et al., "A Simple Way to Reconstruct a Human 3-D Hypodermis: A Useful Tool for Pharmacological Functionality," Skin Pharmacol Physiol, vol. 25, 2012, pp. 47-55.
Marchbank et al., "The CUSP [Delta]Np63[alpha] isoform of human p63 is downregulated by solar-simulated ultraviolet radiation," Journal of Dermatological Science, vol. 32, No. 1, Jun. 2003, pp. 71-74.
Mardis et al., "New strategies and emerging technologies for massively parallel sequencing: applications in medical research," vol. 1, No. 4, 2009, pp. 40.1-40.4.
Metzker, Michael, "Sequencing technologies—the next generation," Nature Reviews: Genetics, vol. 11, Jan. 2010, pp. 31-46.
Paller et al., "New Insights About Infant and Toddler Skin: Implications for Sun Protection", Pediatrics, vol. 128, No. 1, Jun. 2011, pp. 92-102.
Pihlak et al., "Rapid genome sequencing with short universal tiling probes," Nature Biotechnology, vol. 26, No. 6, Jun. 2008, pp. 676-684.
Ponec et al., "Lipid and ultrastructural characterization of reconstructed skin models," International Journal of Pharmaceutics, vol. 203, 2000, pp. 211-225.
Ponec et al., "The Formation of Competent Barrier Lipids in Reconstructed Human Epidermis Requires the Presence of Vitamin C," Journal of Investigative Dermatology, vol. 109, 1997, pp. 348-355.
Poumay et al., "A simple reconstructed human epidermis: preparation of the culture model and utilization in in vitro studies" Arch Dermatol Res. vol. 296, 2004, pp. 203-211.
Rosdy et al., "Retinoic Acid Inhibits Epidermal Differentiation When Applied Topically on the Stratum Corneum of Epidermis Formed In Vitro by Human Keratinocytes Grown on Defined Medium," In Vitro Toxicology, vol. 10, No. 1, 1997, pp. 39-47.
Schmalz et al., "Release of prostaglandin E2, IL-6 and IL-8 from human oral epithelial culture models after exposure to compounds of dental materials," Eur J Oral Sci, vol. 108, 2000, pp. 442-448.
Shendure et al., "Next-generation DNA sequencing," Nature Biotechnol., vol. 26, No. 10, 2008, pp. 1135-1145.
Stanton et al. "Primary prevention of skin cancer: a review of sun protection in Australia and internationally", Health Promotion International, vol. 19, No. 3, 2004, pp. 369-378.
Vahlquist et al., "Markers of Skin Inflammation and Wound healing," Acta Derm Venereol, vol. 80, 2000, p. 161.
Vrana et al., "Development of a Reconstructed Cornea from Collagen-Chondroitin Sulfate Foams and Human Cell Cultures," IOVS, vol. 49, No. 12, Dec. 2008, pp. 5325-5331.
Wolnicka-Glubisz et al., "Neonatal susceptibility to UV induced cutaneous malignant melanoma in a mouse model," Photochemical & Photobiological Sciences, vol. 5, 2006, pp. 254-260.
Wu et al., "IL-8 production and AP-1 transactivation induced by UVA in human keratinocytes: Roles of D-a-tocopherol," Molecular Immunology, vol. 45, 2008, pp. 2288-2296.

A

B

METHOD FOR EVALUATING THE HARMFUL EFFECTS OF UV ON CHILDREN'S SKIN

The present invention relates to in vitro methods for testing formulations or active ingredients to prevent the harmful effects of UV on children's skin, in particular aged three or younger.

Human skin daily undergoes exposure to ultraviolet radiation (UV) which to a certain extent is beneficial for human health.

For example it is well known that exposure to the sun allows synthesis of vitamin D, a deficiency thereof leading to growth disorders. In addition, some dermatoses such as psoriasis, atopic dermatitis and some vitiligo disorders are improved with natural or artificial UV inducing a reduction in these lesions.

Excessive exposure to UV however, whether occasional or chronic, may have pathological consequences on the skin.

Sunburn is the best known acute effect of excessive, occasional UV exposure in strong sunshine for example.

This reaction by the tissues results from cell deterioration at the sites of lesions due to the harmful effects of UV. High intensity UV radiation damages the cells of the skin surface layer.

In its most benign form sunburn leads to reddening of the skin called erythema. This occurs shortly after UV exposure and reaches maximum intensity within the following 8 to 24 hours. It disappears after a few days. However strong sunburn may cause the onset of blisters or cause skin "peeling". The "new" skin thus exposed no longer has the protection of the corneal layer and is therefore particularly delicate. In addition, in the event of strong sunburn the blisters may subsequently leave behind scarring at the lesion site.

Over the long term excessive, chronic UV exposure causes degenerative lesions in the skin cells, fibrous tissue and blood vessels leading to premature ageing of the skin, to photodermatoses and actinic keratoses. Skin cancer, most often in the form of malignant melanoma is the most known degenerative lesion resulting from excessive chronic UV exposure.

The seriousness and frequency of these occasional or chronic skin reactions are not only dependent on the quantity and type of UV to which the skin is exposed, but also on skin type itself. It is well known that skin phototype plays a major role in UV reaction both regarding risk of sunburn and the risk of developing a malignant melanoma.

In addition, it is generally considered that children's skin is particularly sensitive to UV and the more so the younger they are. It is known that children are more likely to develop reactions of "sunburn" type after exposure to UV. It would also seem that sun exposure during childhood determines the onset of skin cancers at adult age (Stanton W R, *Health Promot Int.;* 19(3):369-78; 2004). The skin damage caused by UV could accumulate on and after the first summer of one's life (Palter A S et al, *Pediatrics;* 128: 92-10; 2011).

Before the age of three years, children have practically no defence against the sun. Their as yet immature skin means that they are particularly sensitive to sun rays allowing a large amount of UVA and UVB to pass which attack the basal layers of the epidermis. In animal models it has been shown that UV causes more mutations on the DNA of melanocytes of new-born mice compared with adult mice, thereby generating a greater number of tumours (Wolnicka-Glubisz A and Noonan F P, *Photochem Photobiol Sci.;* 5:254; 2006).

It is therefore generally acknowledged that it is necessary to protect children's skin even though the variety and extent of UV effects at cell and molecular level in this specific skin are not accurately known. For lack of knowledge of the specificities of children's reaction to UV rays, the products developed for adults are conventionally used for children.

However, the inventors have discovered that the skin of very young children i.e. aged three or younger has a specific response to UV exposure. In other words, it is not possible to estimate the reaction of very young skin to UV exposure on the basis of what is known for adult skin.

Thus, the inventors have for example shown that subsequent to UVA and UVB exposure, the expression level of some markers increases or decreases to a large extent in the skin of children aged three years or younger compared with the skin of older children. These modulations (increase or decrease) are not homogeneous for all markers known to be stimulated by UV. Therefore the expression profile of the skin of children aged three or younger cannot in any way be simply extrapolated from results obtained for skin in older children or in adults.

Unfortunately at the current time there is no available method allowing evaluation of the efficacy of sunscreens on the very specific skin of very young children aged three years or younger. As a result the lack of adapted in vitro test methods hampers the development of safe, efficient cosmetic or therapeutic products intended for this age group.

There is therefore a true need for in vitro methods allowing evaluation of the efficacy of formulations or active ingredients in the prevention of the harmful UV effects on the skin of children aged three years or younger.

FIGURE LEGENDS

FIG. 1: histological analysis and analysis of sunburn cell formation in irradiated reconstructed epidermises. ↘ Sunburn (SB) cell (A) non-irradiated, reconstructed 3-month epidermis; (B) UVA+B irradiated reconstructed 3-month epidermis—574 SB Cell/mm$^2$; (C) non-irradiated, reconstructed 11-year epidermis; (D) UVA+B irradiated, reconstructed 11-year epidermis—529 SB Cell/mm$^2$.

Figure 2:
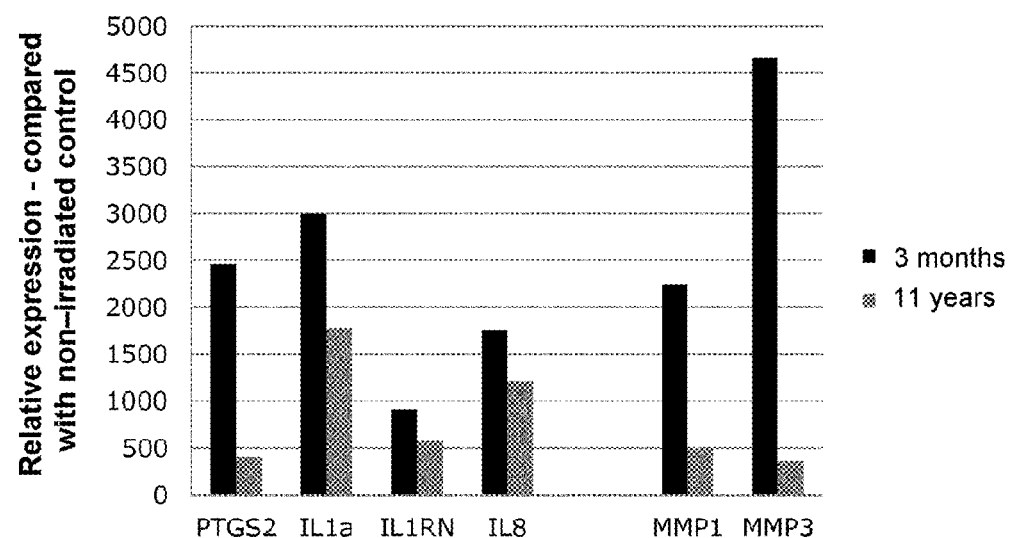

FIG. 2: Profile of UV-induced inflammation genes—Comparison of 3-month and 11-year epidermises.

Figure 3:
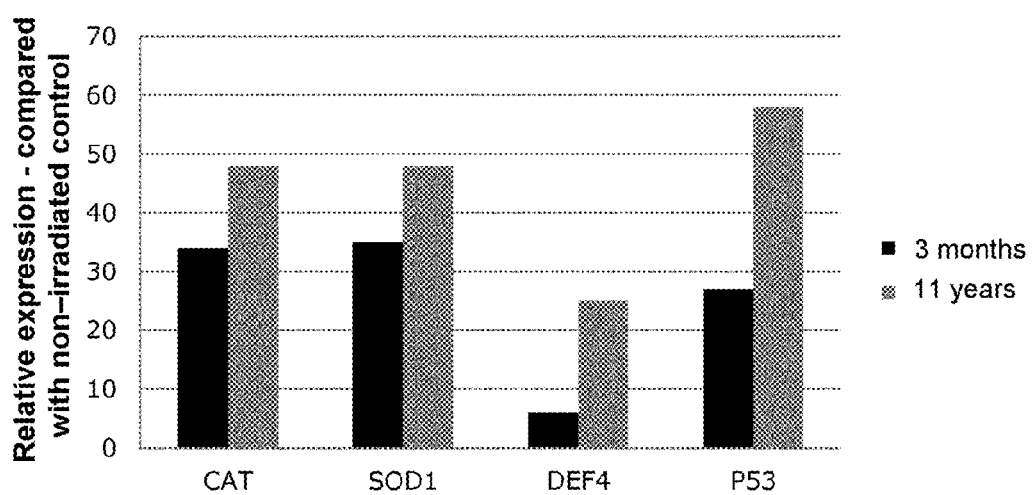

FIG. 3: Profile of antioxidant defence, antimicrobial and DNA protection genes repressed by UVs—Comparison of 3-month and 11-year epidermises.

Figure 4:
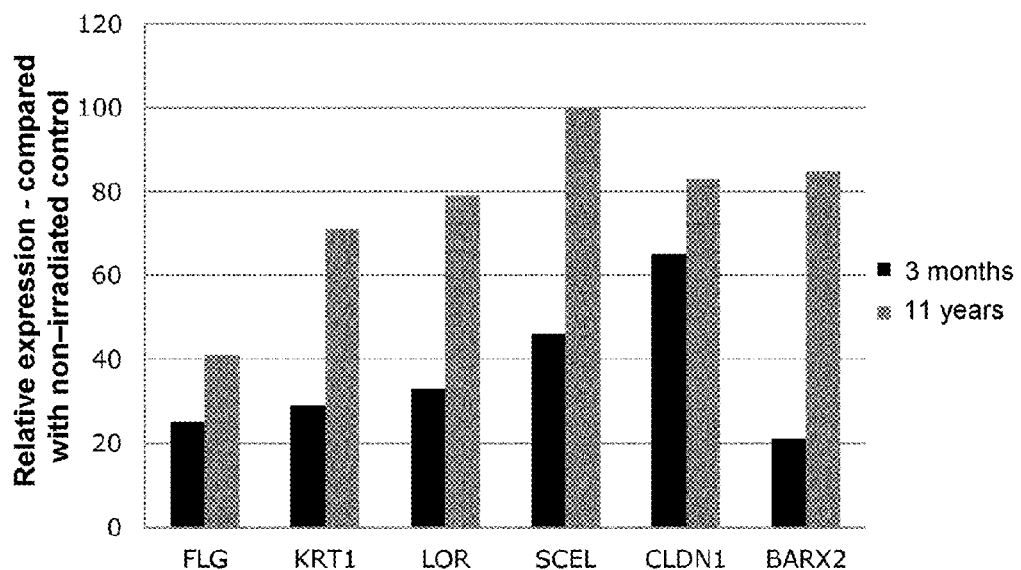

FIG. 4: Profile of epidermal differentiation and barrier function genes repressed by UVs—Comparison of 3-month and 11-year epidermises.

Figure 5:
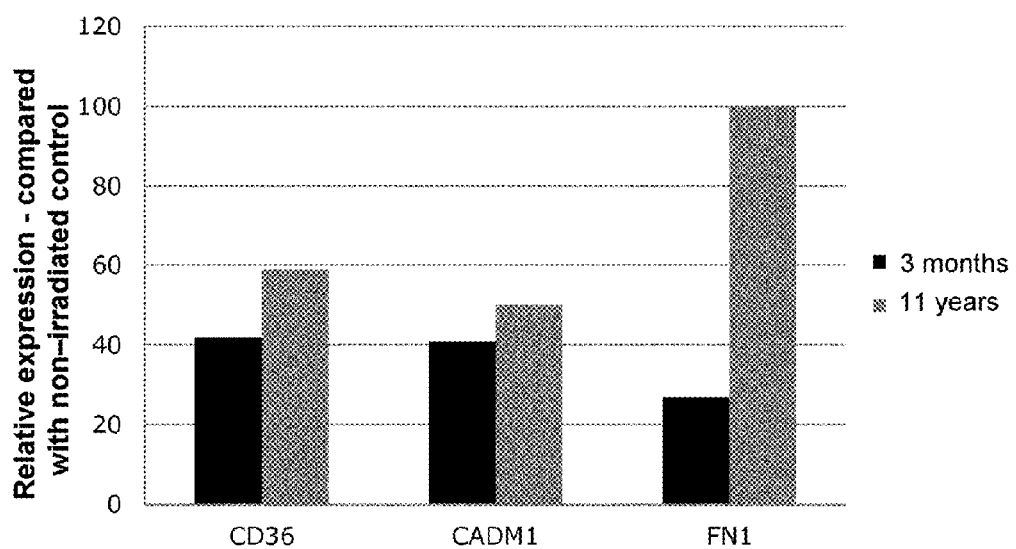

FIG. 5: Profile of cell-cell interaction, matrix adhesion and epidermal repair genes repressed by UVs—Comparison of 3-month and 11-year epidermises.

Figure 6:
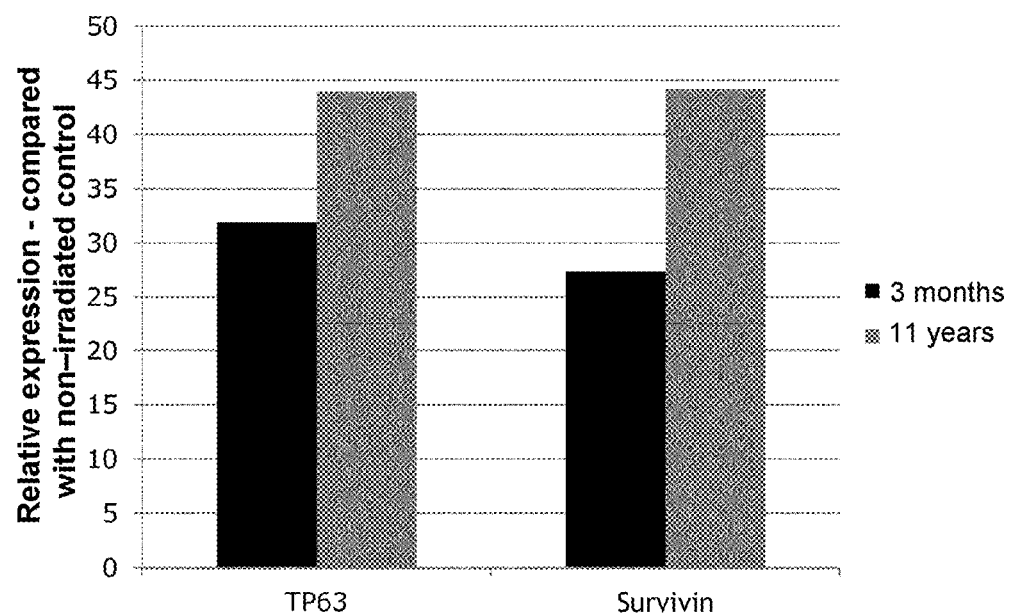

FIG. 6: Profile of stem cell genes suppressed by UVs—Comparison of 3-month and 11-year epidermises.

Figure 7:
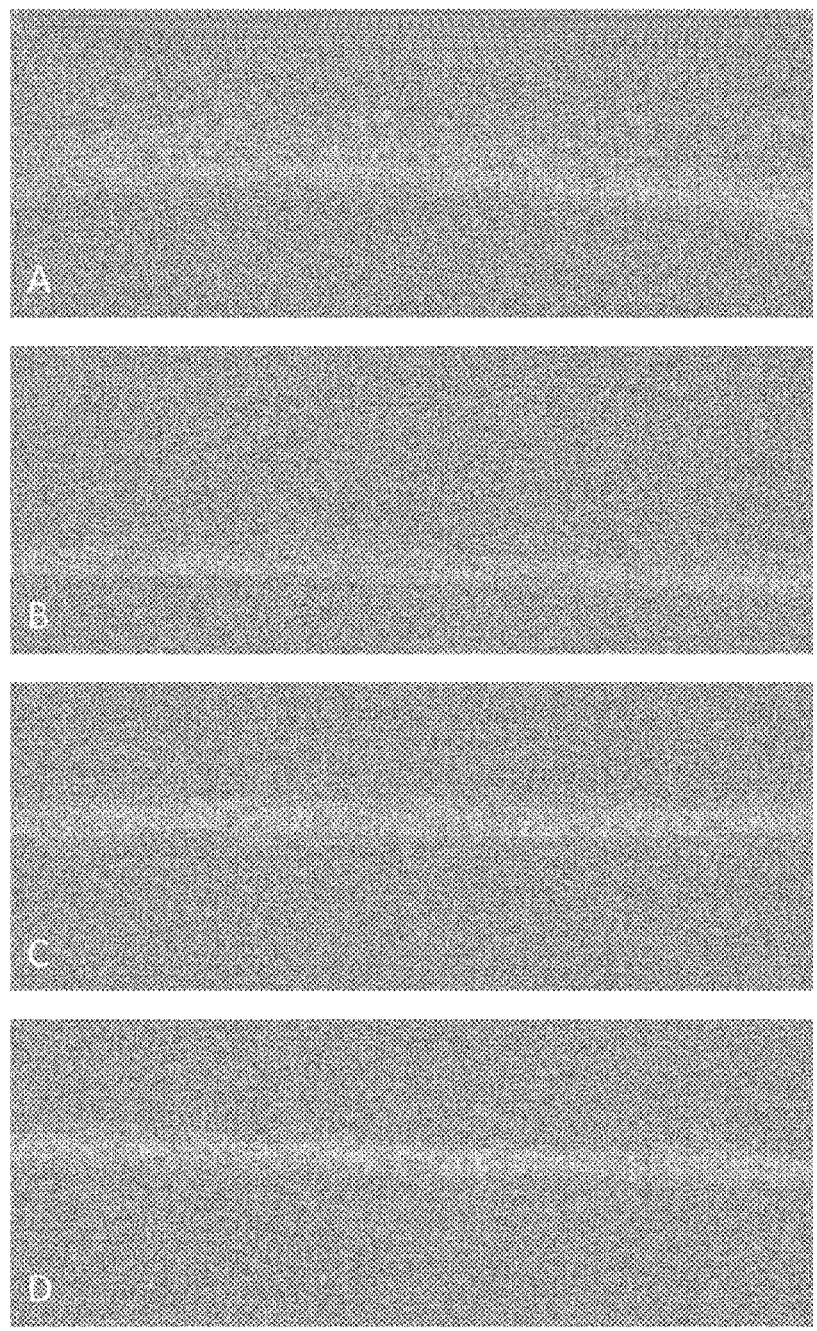

FIG. 7: Immunolabelling of integrin alpha-6 in irradiated reconstructed epidermises. (A) non-irradiated, reconstructed 3-month epidermis; (B) UVA+B irradiated reconstructed 3-month epidermis; (C) non-irradiated reconstructed 11-year epidermis; (D) UVA+B irradiated, reconstructed 11-year epidermis.

Figure 8:
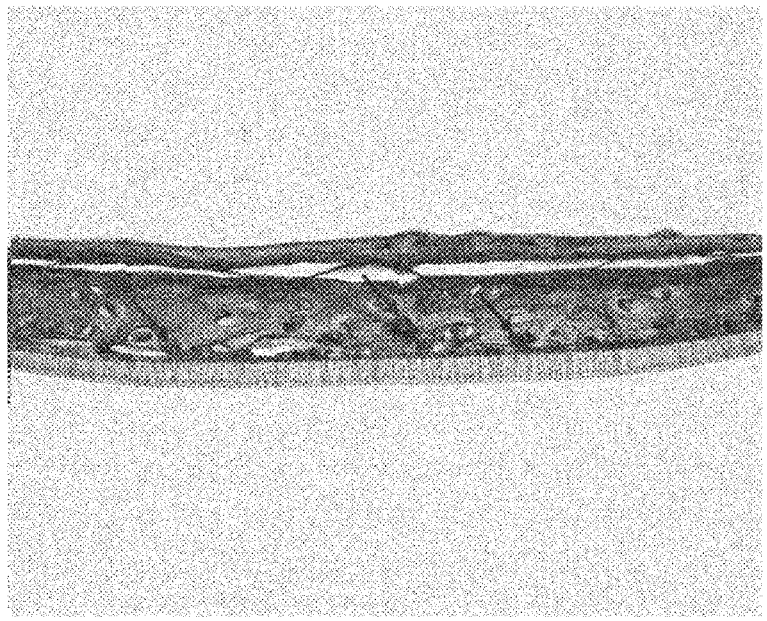
Figure 8:
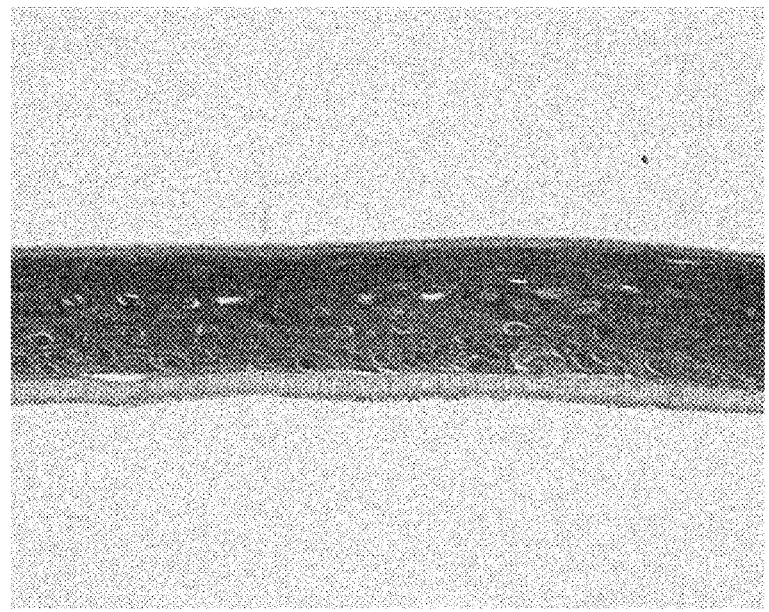

FIG. 8: histological analysis and analysis of sunburn cell formation analysis in irradiated reconstructed 3-month epidermis with or without sun cream containing avocado perseose. ↘ Sunburn (SB) cells (A) UVA+B irradiated reconstructed 3-month epidermis—574 SB Cell/mm², (B) UVA+B irradiated reconstructed 3-month epidermis with sun cream—0 SB cell/mm².

DETAILED DESCRIPTION

The inventors have shown that the skin of very young children i.e. children aged three or younger, preferably aged two or younger, more preferably aged one year or younger, further preferably aged six months or younger and in particular three months or younger, is particularly sensitive to the harmful effects of UV rays. In particular, they have shown that the skin of children aged three years or younger reacts to UVA and/or UVB radiation exposure in different manner not only compared with adult skin but also with the skin of children aged about 11 years. In particular the inventors have evidenced the greater seriousness of the harmful effects of UV rays on a 3-month old epidermis thereby demonstrating the greater sensitivity to sun of the skin in infants and young children.

The inventors have developed methods for in vitro evaluation of the efficacy of formulations in preventing harmful UV effects on the skin of children aged three years or younger, using a skin model specifically capable of reproducing the characteristics of children's skin in this age group. The methods of the invention are therefore based on the use of an adapted skin model reproducing the skin of children aged three or younger, and on the use of biomarkers the expression of which is affected by UV rays in particular manner in the skin of children aged three or younger, preferably two or younger, more preferably one or younger, further preferably six months or younger and in particular aged three months or younger, compared with skin in older children or in adults.

The methods of the invention are also adapted for evaluating the action of active ingredients. With the invention it is therefore possible to determine accurately which active ingredients have an advantageous effect in the prevention or treatment of harmful UV effects on the skin.

According to a first aspect, the subject of the invention is a method to evaluate the in vitro efficacy of a formulation or active ingredient in the prevention of harmful UV effects on the skin of children aged three years or younger, preferably two years or younger, more preferably one year or younger, further preferably six months or younger and in particular three months or younger, characterized in that said method comprises the following steps:
  a) contacting said formulation or said active ingredient with a skin model comprising keratinocytes taken from subjects aged 3 years or younger, preferably two years or younger, more preferably one year or younger, further preferably six months or younger and in particular three months or younger;
  b) exposing the skin model of step a) to UV;
  c) measuring the expression level of at least one biomarker in the skin model of step b), characterized in that said biomarker is selected from among skin inflammation markers;
  d) comparing the expression level of at least one biomarker obtained at step c) with a reference expression level;
  e) evaluating the efficacy of said formulation or said active ingredient in the prevention of harmful UV effects on the skin of children aged three years or younger, preferably two years or younger, more preferably one year or younger, further preferably six months or younger and in particular three months or younger, as a function of the comparison at step d).

By "efficacy of a formulation or active ingredient in the prevention of harmful UV effects on the skin of children aged three years or younger, preferably two years or younger, more preferably one year or younger, further preferably six months or younger and in particular three months or younger" in the meaning of the present application is meant the capability of the formulation or active ingredient to cancel or reduce said harmful effects on the skin of children aged three years or younger, preferably two years or younger, more preferably one year or younger, further preferably six months or younger and in particular three months or younger.

According to another aspect, the invention allows isolating formulations or active ingredients having an effect in the prevention of harmful UV effects on the skin of children aged three years or younger. With the invention it is therefore possible to identify those formulations or active ingredients that are suitable for this highly specific skin.

A further subject of the invention is therefore a method to identify a formulation or active ingredient for the prevention of harmful UV effects on the skin of children aged three years or younger, characterized in that said method comprises the following steps:
  a) contacting a candidate formulation or active ingredient with a skin model comprising keratinocytes obtained from subjects aged three years or younger;
  b) exposing the skin model of step a) to UV;
  c) measuring the expression level of at least one biomarker in the skin model of step b), characterized in that said biomarker is selected from among skin inflammation markers;
  d) comparing the expression level of at least one biomarker obtained at step c) with a reference expression level;
  e) determining whether said candidate formulation or active ingredient is a formulation or active ingredient for the prevention of harmful UV effects on the skin of children aged three year or younger as a function of the comparison at step d).

The candidate formulation is a formulation for the prevention of harmful UV effects on the skin of children aged three years or younger, if said candidate formulation allows modulation of the expression of at least one biomarker of the invention. This modulation according to cases and in particular depending on type of biomarker, may correspond to an increase or decrease of the expression of said marker. For example, it may be of interest to isolate formulations minimising harmful UV effects on markers preferably expressed in stem cells, these formulations allowing the fragile skin of children aged three years or younger to preserve its capacity for epidermal renewal.

Similarly the candidate active ingredient is an active ingredient for the prevention of harmful UV effects on the skin of children aged three years or younger, if said candidate active ingredient allows modulation of the expression of at least one biomarker of the invention. This modulation according to cases and in particular depending on type of biological marker may correspond to an increase or decrease in the expression of said marker.

By "harmful UV effects" in the meaning of the present application is meant pathological reactions resulting from skin exposure to UV rays i.e. UVA and/or UVB. These pathological reactions particularly comprise erythema, the formation of so-called "sunburn cells", deterioration of the barrier and epidermis, the formation of lesions, peeling, deteriorated physiology of stem cells and DNA damage to irradiated cells. As is well known to persons skilled in the art "sunburn cells" are keratinocytes having suffered harmful UV effects. Sunburn cells are apoptotic keratinocytes easily identifiable via histochemical analysis, via their characteristic morphology namely a dark, condensed pycnotic basophilic nucleus, eosinophilic cytoplasm and the formation of intercellular spaces.

In the meaning of the invention "efficacy of a formulation in the prevention of harmful UV effects on the skin of children aged three years or younger, preferably two years or younger, more preferably one year or younger, further preferably six months or younger and in particular three months or younger" is meant the capability of the formulation to decrease at least one of the aforementioned harmful effects.

Initially the formulation of interest is contacted with a skin model comprising keratinocytes obtained from subjects aged three years or younger, preferably two years or younger, more preferably one year or younger, further preferably six months or younger and in particular three months or younger.

Similarly, the contacting of the active ingredient of interest with the skin model can be made directly if the formulation of the active ingredient so permits. In some cases it may be advantageous to formulate the active ingredient of interest to obtain a liquid composition for example, to facilitate the contacting thereof with the skin model. Therefore according to one embodiment of the invention, the method further comprises a step to formulate the active ingredient in the form of a liquid solution in particular, an aqueous form in particular, prior to the contacting step of said active ingredient with a skin model.

In the meaning of the invention the skin model comprising keratinocytes obtained from subjects aged three years or younger, preferably two years or younger, more preferably one year or younger, further preferably six months or younger and in particular three months or younger, may be any tissue model comprising keratinocytes in which the keratinocytes were obtained from subjects aged three years or younger, preferably two years or younger, more preferably one year or younger, further preferably six months or younger and in particular three months or younger.

The inventors have previously shown that the expression profiles of specific gene categories (e.g. barrier, inflammation, defence, stem cell genes) undergo change as a function of age (application PCT/EP2013/064926). Skilled persons are therefore easily able to characterize skin at molecular level from birth up until adult age. More particularly, skilled persons will note that the skin cells including the keratinocytes of a child aged three years or younger exhibit a specific expression profile of the genes involved in particular physiological processes, particularly cell metabolism, response to stress, inflammation, immunity, apoptosis, growth/proliferation and cell cycle, cell signalling, migration and differentiation, epidermal barrier, adhesion and pluripotent skin stem cells.

Therefore the skin model of the invention may be any tissue model comprising keratinocytes obtained from subjects aged three years or younger, preferably two years or younger, more preferably one year or younger, further preferably six months or younger and in particular three months or younger. The skin model of the invention is therefore not strictly limited to a particular type of tissue model and can be adapted to the needs of those skilled in the art.

By "tissue module comprising keratinocytes" in the meaning of the invention is meant any in vitro culture of skin cells at least comprising keratinocytes. Therefore the "tissue models comprising keratinocytes" according to the invention comprise monolayer keratinocyte cultures, bilayer skin cell cultures comprising keratinocytes and tissue models such as cultures of reconstructed skin comprising keratinocytes. Advantageously the skin model comprises cultures of reconstructed skin comprising keratinocytes.

According to the invention the skin cells comprise at least one type of cell usually contained in the hypodermis, dermis and/or epidermis. These cells inter alia therefore comprise keratinocytes, melanocytes, fibroblasts, adipocytes, endothelial cells, mastocytes, Langerhans cells and/or Merkel cells. Preferably the skin cells of the invention comprise at least keratinocytes and/or fibroblasts.

Monolayer or bilayer skin cell cultures are known and have been used for a very long time, and do not require any detailed description.

Additionally, numerous reconstructed skin models are available for those skilled in the art (who can refer in particular to Rosdy et al., In Vitro Toxicol., 10(1): 39-47, 1997; Ponec et al., J Invest Dermatol., 109(3): 348-355, 1997; Ponec et al., Int J Pharm., 203(1-2): 211-225, 2000; Schmalz et al., Eur J Oral Sci., 108(5): 442-448, 2000; Black et al., Tissue Eng, 11(5-6): 723-733, 2005; Dongari-Batgtzoglou and Kashleva, Nat Protoc, 1(4): 2012-2018, 2006; Bechtoille et al., Tissue Eng, 13(11): 2667-2679, 2007; Vrana et al., Invest Ophthalmol Vis Sci, 49(12): 5325-5331, 2008; Kinicoglu et al., Biomaterials, 30(32): 6418-6425, 2009; Auxenfans et al., Eur J Dermatol, 19(2): 107-113, 2009; Kinicoglu et al., Biomaterials, 32(25): 5756-5764, 2011; Costin et al., Altern Lab Anim, 39(4): 317-337, 2011; Auxenfans et al., J Tissue Eng Regen Med, 6(7): 512-518, 2012; Lequeux et al., Skin Pharmacol Physiol, 25(1): 47-55, 2012; EP 29 678; EP 285 471; EP 789 074; EP 1 451 302 B1; EP 1 878 790 B1; EP 1 974 718; US 2007/0148,771; US 2010/0,099,576; WO 02/070729; WO 2006/063864; WO 2006/0,63865; WO 2007/064305).

Preferably the reconstructed skin model is selected from the group comprising epidermal models chiefly formed of keratinocytes, skin models comprising a dermis and epidermis, and skin models comprising a hypodermis, dermis and epidermis. The models comprising at least an epidermis form stratified epithelia comprising the characteristic layers of the tissue under consideration. For example in epidermis models it is possible to identify a basal layer (*stratum basalis*), spinous layer (*stratum spinosum*), granular layer (*stratum granulosum*) and horny layer (*stratum corneum*).

Advantageously the skin model of the invention is an epidermis model comprising a matrix substrate preferably selected from among:

an inert substrate selected from the group consisting of a semi-permeable synthetic membrane, in particular a semi-permeable nitrocellulose membrane, a semi-permeable nylon membrane, a membrane or sponge in Teflon, a semi-permeable membrane in polycarbonate or polyethylene, in polypropylene, polyethylene terephthalate (PET), a semi-permeable Anopore inorganic membrane, in acetate or cellulose ester (HATF), a semi-permeable Biopore-CM membrane, semi-permeable polyester membrane.

This group includes the reconstructed Epiderme model (Skinethic®) and EpiDerm® model (Mattek Corporation);

a film, membrane or matrix containing hyaluronic acid and/or collagen and/or fibronectin and/or fibrin.

Within this group particular mention can be made of the models: Laserskin® (Fidia Advanced Biopolymers), Episkin® (L'Oréal).

In addition, these models may or may not be seeded with fibroblasts in the dermal part.

Advantageously the following can be added to the skin model of the invention: pigment cells, immunocompetent cells, nerve cells, preferably the immunocompetent cells are Langerhans cells. In general, if the skin model of the invention is an epidermis model the matrix substrate is produced and then seeded with the keratinocytes of the invention to reconstruct the epidermis and finally obtain a reconstructed skin comprising keratinocytes.

In the context of the invention the term "keratinocytes" designates both primary keratinocytes and immortalised keratinocytes e.g. keratinocytes derived from cell lines.

According to the invention the primary or immortalised keratinocytes are of human origin. For example the keratinocytes are derived from biological samples taken from a human subject aged three years or younger, preferably two years or younger, more preferably one year or younger, further preferably six months or younger and in particular three months or younger. Evidently however by the expression "obtained from subjects aged three years or younger, preferably two years or younger, more preferably one year or younger, further preferably six months or younger and in particular three months or younger", the present application does not refer to keratinocytes sampled in utero, or in unborn subjects. The present invention therefore clearly excludes the use of embryonic cells.

Human keratinocytes can be isolated in particular from skin samples using cell culture techniques well known to skilled persons.

For example, keratinocytes may be keratinocytes obtained from an explant of skin tissue, in particular samples of keratinised Malpighian epithelium. Human keratinocytes can then be easily cultured in vitro using well-known techniques. Skilled persons can refer in particular to Leigh et al. (*Arch Dermatol Res.;* 286(1):53-61.1994).

By "explant" or "skin explant" is meant herein a cell or skin tissue sample which can be taken for therapeutic purposes or to perform analyses.

In particular, an explant can be obtained during surgical excision. By "excision" is meant herein surgical procedure to cut out (excise) a piece of skin of greater or lesser width or depth to treat an anomaly or outgrowth. Excision is performed for example either to remove a tumour that is cancerous or suspected of being cancerous, or to treat a benign anomaly of the skin causing discomfort, whether for functional or cosmetic reasons. Excision in the meaning of the invention includes for example a skin sample obtained after plastic surgery (mammary, abdominal plasty, lifting, foreskin removal, otoplasty i.e. ear pinning, finger syndactyly or polydactyly, etc.).

An explant may also be obtained by biopsy. By "biopsy" is meant herein a cell or skin tissue sample taken for analysis. Several types of biopsy procedures are known and performed in this field. The most frequent types comprise (1) incisional biopsy whereby solely a tissue sample is taken; (2) excisional biopsy (or surgical biopsy) for full ablation of a tumoral mass thereby obtaining a therapeutic and diagnostic result, and (3) needle biopsy to obtain a tissue sample using a thin or thick needle. There are other types of biopsy e.g. smears or curettage and are also encompassed within the present invention.

By "immortalised keratinocytes" in the present invention is meant keratinocytes which divide beyond the Hayflick limit. These cells have therefore acquired the capability of multiplying indefinitely either subsequent to random mutation or to deliberate modification.

It is well known that normal cells can only divide a determined number of times. Once this limit is reached the cells become senescent and die. The Hayflick limit corresponds to the number of divisions which can be made by a normal cell i.e. a cell only able to divide a determined number of times before ceasing to divide. In the meaning of the present invention the Hayflick limit corresponds to the number of divisions able to be carried out by a normal keratinocyte before ceasing to divide.

Keratinocytes can be immortalised further to particular anomalies as is the case for example with cancer cells or after implementing an immortalisation technique. Immortalisation techniques are well known to skilled persons and it is easily within their reach to select the technique best adapted for intended purpose. For example, and without limiting the invention thereto, as immortalisation technique mention can be made of transformation by an oncogene, in particular by antigen T of SV40, the Ras protein, myc protein, Abl protein. As other techniques for example the overexpression of telomerase reverse transcriptase can be cited e.g. hTERT, or confluency keratinocyte culture passaged several times. All these techniques are conventional cell biology techniques which do not need to be detailed herein.

After contacting the formulation of interest with the skin model of the invention, skilled persons can expose this treated skin model to UV.

By "expose the skin model to UV" in the meaning of the invention is meant any exposure to radiation comprising or consisting of ultraviolet rays.

In the meaning of the invention, the terms "ultraviolet rays" refer to electromagnetic rays having wavelengths between 153 nm and 400 nm. Preferably exposure to UV according to the invention comprises exposure to UVA and/or UVB. By UVA in the meaning of the invention is meant radiation having a wavelength between 400 and 315 nm. By UVB in the meaning of the invention is meant radiation having a wavelength between 315 and 280 nm.

Therefore according to one preferred embodiment, exposure to UV according to the invention comprises or consists of exposure to UVA. According to another preferred embodiment, exposure to UV comprises or consists of exposure to UVB. According to one advantageous embodiment exposure to UV according to the invention comprises or consists of exposure to UVA and UVB.

The exposure of an in vitro model to UV is a routine technique well known to those skilled in the art. In the meaning of the invention this exposure can be obtained following any method chosen by skilled persons. Such persons may in particular refer to Diffey B L et al. (*J Am Acad Dermatol;* 43(6):1024-35; 2000) regarding standard methods for UV exposure used in the cosmetic field.

After exposing the skin model of the invention to UV rays skilled persons can subsequently measure the expression levels of the biomarkers of the invention.

By "biomarker" in the meaning of the present application is meant a characteristic which is objectively measured and evaluated as an indicator of normal biological processes, pathogenic processes or pharmacological responses to therapeutic action. A biomarker therefore designates a whole range of various substances and parameters. For example a biomarker may be a substance the detection of which indicates a particular pathological condition (e.g. the presence of activated protein C as marker of an infection) or on the contrary a substance the detection of which indicates a specific physiological condition. The biomarker of the invention is preferably a gene, the products of a gene such as the transcripts thereof and peptides derived from its transcripts, a lipid, sugar or metabolite.

According to one embodiment of the present invention the biomarker is a gene, the products of a gene such as transcripts or peptides, a lipid, sugar or metabolite of which changes in expression in particular expression level correlate with a physiological skin condition of children aged three years or younger, preferably two years or younger, more preferably one year or younger, further preferably six months or younger and in particular aged three months or younger. According to one particular embodiment, the biomarker is a peptide having enzymatic activity.

The inventors have evidenced that the markers of skin inflammation can be used to observe the reaction of the skin of children aged three years or younger, preferably two years or younger, more preferably one year or younger, further preferably six months or younger and in particular aged three months or younger, after exposure to UV.

By "skin inflammation markers" in the meaning of the invention is meant markers for which variation in expression correlates with skin inflammation.

Skin inflammation is a reaction of the immune system well known to skilled persons which manifests as erythema characterized by redness associated with local vasodilatation, oedema characterized by swelling and feeling of heat. In addition, skin inflammation is accompanied by variation in the expression level or concentration of gene or protein markers well known to skilled persons who can refer for example to Vahlquist (*Acta Derm Venereol;* 80: 161; 2000).

Persons skilled in the art seeking to determine the class to which a gene or protein marker belongs are easily able to consult relevant scientific literature or public databases such as those for example grouped on the website of the National Center for Biotechnology Information (http://www.ncbi.nlm.nih.gov/guide/).

The inventors have particularly selected markers for which the expression level varies after UV exposure in surprising and unexpected manner in children aged three years or younger, preferably two years or younger, more preferably one year or younger, further preferably six months or younger and in particular aged three months or younger. The expression profile of these markers is particular interest in that it largely and unpredictably differs from the expression profile observed in models of adult skin or of children aged about 11 years.

The selected markers are therefore of particular interest for the method of the invention insofar as their expression level is measured on a skin model reproducing the characteristics of a child's skin aged three years or younger.

According to the invention the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3.

In the meaning of the present invention the biomarker PTGS2 comprises the human PTGS2 gene (NCBI reference: Gene ID: 5743) and the products of this gene. In one particular embodiment, the PTGS2 biomarker is the human PTGS2 gene (NCBI reference: Gene ID: 5743). According to another embodiment the PTGS2 biomarker is one of the products of the human PTGS2 gene. The products of the PTGS2 gene comprise the transcript of the human PTGS2 gene and the human protein prostaglandin-endoperoxide synthase 2, also known under the name cyclo-oxygenase-2 or COX-2. In the meaning of the present invention the transcript of the human PTGS2 gene is the polynucleotide having the sequence with NCBI reference: NM_000963. By "human COX-2" in the meaning of the invention is meant the protein for which the peptide sequence carries NCBI reference: NP_000954.

In the meaning of the present invention, the IL1α biomarker comprises the human IL1A gene (NCBI reference: Gene ID: 3552) and the products of this gene. In one particular embodiment the IL1α biomarker is the human IL1A gene (NCBI reference: Gene ID: 3552). According to another embodiment the IL1A biomarker is one of the products of the human IL1A gene. The products of the human IL1A human gene comprise the transcript of the human IL1A gene and the human protein IL1α. In the meaning of the invention the transcript of the human IL1A gene is the polynucleotide having the sequence with NCBI reference: NM_000575. By "human IL1α protein" in the meaning of the invention is meant the protein having the peptide sequence that is the sequence with NCBI reference: NP_000566

In the meaning of the present invention the IL8 biomarker comprises the human IL8 gene (NCBI reference: Gene ID: 3576) and the products of this gene. In one particular embodiment, the IL8 biomarker is the human IL8 gene (NCBI reference: Gene ID: 3576). According to another embodiment the IL8 biomarker is one of the products of the human IL8 gene. The products of the human IL8 gene comprise the transcript of the human IL8 gene and the human IL8 protein. In the meaning of the present invention the "transcript of the human IL8 gene" is the polynucleotide having the sequence with NCBI reference: NM_000584. By "human IL8 protein" in the meaning of the invention is meant the protein having the peptide sequence with NCBI reference: NP_000575.

In the meaning of the present invention the IL1-R1 biomarker comprises the human IL1-R1 gene (NCBI reference: Gene ID: 3554) and the products of this gene. In one particular embodiment the IL1-R1 biomarker is the human IL1-R1 gene (NCBI reference: Gene ID: 3554). According to another embodiment the IL1-R1 biomarker is one of the products of the human IL1-R1 gene. The products of the human IL1-R1 gene comprise the transcript of the human IL1-R1 gene and the precursor of the human IL1-R1 protein. In the meaning of the present invention the transcript of the human IL1-R1 gene is the polynucleotide having the sequence with NCBI reference: NM_000877.2. By "precursor of the human IL1-R1 protein" in the meaning of the invention is meant the protein having the peptide sequence with NCBI reference: NP_000868.1.

In the meaning of the present invention the IL1-RN biomarker comprises the human IL1RN gene (NCBI reference: Gene ID: 3557) and the products of this gene. In one particular embodiment the IL1-RN biomarker is the human IL1-RN gene (NCBI reference: Gene ID: 3557). According to another embodiment the IL1-RN biomarker is one of the products of the human IL1-RN gene. The products of the IL1-RN gene comprise the transcript of the human IL1-RN gene and the human IL-1RA protein. In the meaning of the present invention the transcript of the human IL1-RN gene is the polynucleotide having the sequence with NCBI reference: NM_000577. By "human IL-1RA protein" in the meaning of the invention is meant the protein having the peptide sequence with NCBI reference: NP_000568.1.

In the meaning of the present invention the MMP1 biomarker comprises the human MMP1 gene (NCBI reference: Gene ID: 3557) and the products of this gene. In one particular embodiment the MMP1 biomarker is the human MMP1 gene (NCBI reference: Gene ID: 4312). According to another embodiment the MMP1 biomarker is one of the products of the human MMP1 gene. The products of the human MMP1 gene comprise the transcript of the human MMP1 gene and the human MMP1 protein. In the meaning of the present invention the transcript of the human MMP1 gene is the polynucleotide having the sequence with NCBI reference: NM_001145938. By "human MMP1 protein" in the meaning of the invention is meant the protein having the peptide sequence with NCBI reference: NP_001139410.

In the meaning of the present invention the MMP3 biomarker comprises the MMP3 gene (NCBI reference: Gene ID: 4314) and the products of this gene. In one particular embodiment the MMP3 biomarker is the human MMP3 gene (NCBI reference: Gene ID: 4314). According to another embodiment the MMP3 biomarker is one of the products of the human MMP3 gene. The products of the human MMP3 gene comprise the transcript of the human MMP3 gene and the human MMP3 protein. In the meaning of the present invention the transcript of the human MMP3 gene is the polynucleotide having the sequence with NCBI reference: NM_002422. By "human MMP3 protein" in the meaning of the invention is meant the protein having the peptide sequence with NCBI reference: NP_002413.

In addition, the skilled person will understand that it is possible in the invention to measure other relevant biomarkers. The use of additional biomarkers can therefore allow more complete evaluation of the efficacy of the formulation or active ingredients of interest. In the meaning of the invention relevant biomarkers are for example biomarkers known to be expressed in the skin after UV exposure.

In particular, as detailed in the experimental section, the inventors have shown that antioxidant defence, antimicrobial or DNA markers, epidermal barrier markers, skin adhesion and repair markers and markers preferably expressed in stem cells are expressed differently in models of baby skin exposed to UV rays and in skin models of children aged about 11 years treated under the same conditions.

These markers can therefore be given advantageous use in the methods of the invention.

Therefore, according to one preferred embodiment, the method of the invention is characterized in that step c) further comprises the measurement of at least one biomarker selected from the group consisting of:
 antimicrobial antioxidant defence or DNA markers, said antioxidant defence or antimicrobial defence marker preferably being selected from the group consisting of catalase, superoxide dismutase 1, defensins in particular the β4 defensin, the p3 tumour suppressor protein; and
 markers of the epidermal barrier, said epidermal barrier marker preferably being selected from the group consisting of filaggrin, keratin 1, sciellin, loricrin, claudin 1, barx2; and
 markers of skin adhesion and repair, said skin adhesion and repair marker preferably being selected from among cell adhesion molecule 1, molecule CD36, fibronectin 1; and
 markers preferably expressed in stem cells, said marker preferably expressed in stem cells preferably being selected from the p63 tumour suppressor protein, survivin.

It will be obvious for persons skilled in the art that the method of the invention will allow evaluation of the efficacy of the formulation or active ingredient that is all the more complete the greater the number of markers of different types used.

According to one particular embodiment the method of the invention is characterized in that step c) comprises measurement of the level of expression of a combination of biomarkers comprising or consisting of:
 at least one skin inflammation marker, where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one antioxidant defence, antimicrobial or DNA marker, said antioxidant defence or antimicrobial marker preferably being selected from the group consisting of catalase, superoxide dismutase 1, defensins in particular the β4 defensin, the p53 tumour suppressor protein; or
 at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one marker of the epidermal barrier, said epidermal barrier marker preferably being selected from the group consisting of filaggrin, keratin 1, sciellin, loricrin, claudin 1, barx2; or
 at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a an MMP3, and at least one marker of skin adhesion and repair, said skin adhesion and repair marker preferably being selected from among cell adhesion molecule 1, molecule CD36, fibronectin 1; or
 at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3 and at least one marker preferably expressed in stem cells, said marker preferably expressed in stem cells preferably being selected from among the p63 tumour suppressor protein and survivin; or According to one particular embodiment the method of the invention is characterized in that step c) comprises measurement of the level of expression of a combination of biomarkers comprising or consisting of:
 at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3 and at least one antioxidant defence, antimicrobial or DNA marker, said antioxidant defence or antimicrobial marker preferably being selected from the group consisting of catalase, superoxide dismutase 1, defensins in particular the β4 defensin, the p53 tumour suppressor protein and at least one marker of the epidermal barrier, said epidermal barrier marker preferably being selected from the group consisting of filaggrin, keratin 1, sciellin, at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3 and at least one antioxidant defence, antimicrobial or DNA marker, said antioxidant defence or antimicrobial marker preferably being selected from the group consisting of catalase, superoxide dismutase 1, defensins in particular defensin β4, the p53 tumour suppressor protein, and at least one marker of skin adhesion and repair, said skin adhesion and repair marker preferably being selected from among cell adhesion molecule 1, the CD36 molecule, fibronectin 1; or at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one antioxidant defence, antimicrobial or DNA marker, said antioxidant defence or antimicrobial marker preferably being selected from the group consisting of catalase, superoxide dismutase 1, defensins in particular defensin β4, the p53 tumour suppressor protein, and at least one marker preferably expressed in stem cells, said marker preferably expressed in stem cells preferably being selected from among the p63 tumour suppressor protein and survivin; or at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one marker of the epidermal barrier, said epidermal barrier marker preferably being selected from the group consisting of filaggrin, keratin 1, sciellin, loricrin, claudin 1, barx2, and at least one marker of skin adhesion and repair, said skin adhesion and repair marker preferably being selected from among cell adhesion molecule 1, molecule CD36, fibronectin 1; or at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one marker of the epidermal barrier said epidermal barrier marker preferably being selected from the group consisting of filaggrin, keratine1, sciellin, loricrin, claudin 1, barx2, and at least one marker preferably expressed in stem cells, said marker preferably expressed in stem cells preferably being selected from among the p63 tumour suppressor protein and survivin; or at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one marker of skin adhesion and repair, said skin adhesion and repair marker preferably being selected from among cell adhesion molecule 1 molecule CD36, fibronectin 1, and at least one marker preferably expressed in stem cells, said marker preferably expressed in stem cells preferably being selected from among the p63 tumour suppressor protein and survivin.

According to one particular embodiment, the method of the invention is characterized in that step c) comprises measurement of the expression level of a combination of biomarkers comprising or consisting of:

at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one antioxidant defence, antimicrobial or DNA marker, said antioxidant defence or antimicrobial marker preferably being selected from the group consisting of catalase, superoxide dismutase 1, defensins in particular defensin β4, the p53 tumour suppressor protein, and at least one marker of the epidermal barrier, said epidermal barrier marker preferably being selected from the group consisting of filaggrin, keratin 1, sciellin, loricrin, claudin 1, barx2, and at least one marker of skin adhesion and repair, said skin adhesion and repair marker preferably being selected from among cell adhesion molecule 1, molecule CD36, fibronectin 1; or at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one antioxidant defence, antimicrobial or DNA marker, said antioxidant defence or antimicrobial marker preferably being selected from the group consisting of catalase, superoxide dismutase 1, defensins in particular defensin β4, the p53 tumour suppressor protein, and at least one marker of skin adhesion and repair, said skin adhesion and repair marker preferably being selected from among cell adhesion molecule 1, molecule CD36, fibronectin 1, and at least one marker preferably expressed in stem cells, said marker preferably expressed in stem cell preferably being selected from among the p63 tumour suppressor protein and survivin; or at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one antioxidant defence, antimicrobial or DNA marker, said antioxidant defence or antimicrobial marker preferably being selected from the group consisting of catalase, superoxide dismutase 1, defensins in particular defensin β4, the p53 tumour suppressor protein, and at least one marker of the epidermal barrier, said epidermal barrier marker preferably being selected from the group consisting of filaggrin, keratin 1, sciellin, loricrin, claudin 1, barx2, and at least one marker preferably expressed in stem cells, said marker preferably expressed in stem cells preferably being selected from among the p63 tumour suppressor protein and survivin; or at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3, and at least one marker of the epidermal barrier said epidermal barrier marker preferably being selected from the group consisting of filaggrin, keratin 1, sciellin, loricrin, claudin 1, barx2, and at least one marker of skin adhesion and repair, said skin adhesion and repair marker preferably being selected from among cell adhesion molecule 1, molecule CD36, fibronectin 1, and at least one marker preferably expressed in stem cells, said marker preferably expressed in stem cells preferably being selected from among the p63 tumour suppressor protein and survivin.

The use of combinations of markers comprising at least one marker of each of the different types indicated above is of particular advantage.

Therefore, according to one preferred embodiment, the method of the invention is characterized in that step c) comprises measurement of the level of expression of a combination of biomarkers comprising or consisting of:
  at least one skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 a and MMP3; and
  at least one antioxidant defence, antimicrobial or DNA marker, said antioxidant defence or antimicrobial marker preferably being selected from the group consisting of catalase, superoxide dismutase 1, defensins in particular defensin β4, the p53 tumour suppressor protein; and
  at least one marker of the epidermal barrier, said epidermal barrier marker preferably being selected from the group consisting of filaggrin, keratin 1, sciellin, loricrin, claudin 1, barx2; and
  at least one marker of skin adhesion and repair, said skin adhesion and repair marker preferably being selected from among cell adhesion molecule 1, molecule CD36, fibronectin 1; and
  at least one marker preferably expressed in stem cells, said marker preferably expressed in stem cells preferably being selected from among the p63 tumour suppressor protein and survivin.

The inventors have particularly shown that the use of all the markers of the invention allows very accurate evaluation of the efficacy of a formulation or active ingredient for the prevention of harmful UV effects on the skin of children aged three years or younger.

Therefore, according to one particularly preferred embodiment, the method of the invention is characterized in that step c) comprises measurement of the expression level of a combination of biomarkers comprising or consisting of PTGS2, IL1α, IL8, IL1-R, IL1-RN, MMP1, MMP3, catalase, superoxide dismutase 1, defensin β4, p53 tumour suppressor protein, filaggrin, keratin 1, sciellin, loricrin, claudin 1, barx2, cell adhesion molecule 1, molecule CD36, fibronectin 1, p63 tumour suppressor protein and survivin.

For each of these markers the terms "expression level" preferably refer to the extent of synthesis of at least one of the products of the gene of said marker.

More specifically, the expression level of said biomarker corresponds to the quantity or cell concentration of the transcript of said gene or of the protein derived from said transcript. According to one embodiment the expression level of said biomarker corresponds to the quantity or cell concentration of the transcript of said gene. According to another embodiment the expression level of said biomarker corresponds to the quantity or cell concentration of the protein derived from said transcript.

By "measurement of the expression level of a combination of biomarkers" in the meaning of the present application is meant measurement of the expression level of each of the markers in the combination. The expression of a gene can be measured for example at nucleotide level, by measuring the number of transcripts of said gene and can also be measured for example at peptide level by measuring the number of proteins derived from said transcripts for example. Therefore by "measurement of the expression level of said gene" in the meaning of the invention is meant measurement of the amount of product of the gene in its peptide form or nucleotide form.

The method of the invention may therefore comprise one or more steps prior to measurement of the expression of the biomarker, said steps corresponding to extraction from a nipple skin model obtained at step a) of a mRNA sample (or corresponding cDNA) or of a protein sample. This can then be directly used to measure expression of the marker. The preparation or extraction of mRNA (and retrotranscription thereof to cDNA) or of proteins from a tissue such as a skin model or from cells are routine procedures well known to skilled persons.

For each of the types of biomarkers of the invention numerous methods are available to skilled persons for measuring the expression level of said biomarker.

When the expression level of the marker is measured at nucleotide level e.g. by measuring the amount of gene product in its nucleotide form, any technology usually used by skilled persons to measure nucleotide quantities can be applied. Methods for analysing the expression level of genes at nucleotide level such as transcriptome analysis for example include well known methods such as RT-PCR or quantitative RT-PCR or nucleic acid chips. By "nucleic acid chips" is meant herein several different nucleic acid probes attached to a substrate which may be a microchip, glass slide or bead of microspheric size. The microchip can be formed of polymers, plastics, resins, polysaccharides, silica or silica-based material, carbon, metals, inorganic glass or nitrocellulose. The probes may be nucleic acids such as cDNA ("cDNA chip"), mRNA ("mRNA chip") or oligonucleotides ("oligonucleotide chip"), said oligonucleotides typically having a possible length of about 25 and 60 nucleotides. To determine the expression profile of a particular gene, a nucleic acid corresponding to all or part of said gene is labelled then contacted with the chip under hybridization conditions, leading to the formation of complexes between said labelled target nucleic acid and the probes attached to the surface of the chip which are complementary to this nucleic acid. The presence of labelled hybridized complexes is then detected.

Preferably the invention is implemented using any current or future method allowing determination of the expression of genes on the basis of quantity of mRNA in a sample. For example, skilled persons can measure the expression of a gene by hybridization with a labelled nucleic acid probe such as Northern blot for example (for mRNA) or Southern blot (for cDNA) but also using techniques such as the serial analysis of gene expression (SAGE) and the derivatives thereof such as LongSAGE, SuperSAGE, DeepSAGE, etc. It is also possible to use tissue chips (also known as TMAs: "tissue microarrays"). The assays usually performed with tissue chips comprise immunohistochemistry and in situ fluorescent hybridization. For analysis at mRNA level, tissue chips can be coupled with in situ fluorescent hybridization. Finally it is possible to use massive parallel sequencing to determine the amount of mRNA in the sample (RNA-Seq or "Whole Transcriptome Shotgun Sequencing"). For this purpose several massive parallel sequencing methods are available. Such methods are described for example in U.S. Pat. No. 4,882,127, U.S. Pat. No. 4,849,077; U.S. Pat. No. 7,556,922; U.S. Pat. No. 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure Et Ji, Nat Biotechnol., 26(10): 1135-45. 2008; Pihlak et al., Nat Biotechnol., 26(6): 676-684, 2008; Fuller et al., Nature Biotechnol., 27(11): 1013-1023, 2009; Mardis, Genome Med., 1(4): 40, 2009; Metzker, Nature Rev. Genet., 11(1): 31-46, 2010.

When the expression level of the marker is measured at peptide level i.e. by measuring the amount of gene product in peptide form, any method to determine the expression level of a polypeptide known to skilled persons can be used. The methods for determining the expression level of a polypeptide include mass spectrometry for example or biochemical assays including immunological assays such as conventional detection immunological assays (ELISA assays and ELISPOTS assays) or immunological assays using protein transfers for example on a substrate such as slot blot (also called dot blot) or western blot. For example it is possible to use protein microarrays, antibody microarrays or tissue microarrays coupled to immunohistochemistry. The other techniques which can be used include FRET or BRET techniques, microscopy or histochemistry methods in particular confocal microscopy and electronic microscopy, methods based on the use of one or more excitation wavelengths and a suitable optical method such as an electrochemical method (voltammetry and amperometry techniques), atomic force microscopy and radiofrequency methods such as confocal and non-confocal multipolar resonance spectroscopy, fluorescence detection, luminescence, chemiluminescence, absorbance, reflectance, transmittance and birefringence or refractive index (e.g. by surface plasmon resonance, by ellipsometry, resonant mirror method etc.), flow cytometry, radioisotope or magnetic resonance imaging, polyacrylamide gel electrophoresis (SDS-PAGE); HPLC-Mass spectrophotometry, liquid chromatography-mass photospectrometry/mass spectrometry (LC-MS/MS). All these techniques are well known to the skilled person and do not require further detailing herein. By "reference expression level of a biomarker" according to the present application is meant any expression level of said marker used as a reference. For example a reference expression level can be obtained by measuring the expression level of the marker of interest in a skin model comprising keratinocytes obtained from subjects aged three years or younger under particular conditions. Skilled persons are able to choose these particular conditions as a function of intended purpose when implementing the invention.

For example, in one preferred embodiment the reference expression level of a biomarker is the expression level of said marker obtained in a skin model comprising keratinocytes obtained from subjects aged three years or younger, non-treated with the formulation or active ingredient of interest, and exposed to UV.

According to another embodiment, the reference expression level of a biomarker is the expression level of said marker obtained in a skin model comprising keratinocytes obtained from subjects aged three years or younger, contacted with a formulation or active ingredient of interest, and exposed to UV.

When the reference expression level is an expression level obtained in a skin model exposed to UV, skilled persons will easily understand that the conditions of UV exposure for the skin model used in the method of the invention and the model used to obtain a reference expression level are preferably the same. Therefore, preferably, the wavelength of the UV radiation used and the exposure time applied in the method of the invention and for the model used to obtain a reference expression level are preferably the same.

For example skilled persons, as reference formulation, can use any formulation known in the prior art for its effect in the prevention of harmful UV effects on skin.

Preferably the reference formulation is selected from among a high protection spray, sun protection milk and sun protection cream. Further preferably the high protection spray corresponds to the formulation in Table 1, the sun protection milk to the formulation in Table 2 and the sun protection cream to the formulation Table 3.

TABLE 1

| High protection spray | |
|---|---|
| Raw material/Trade name | % |
| MIGLYOLGELB | 1 to 10% |
| COPRA CAPRYLATE/CAPRATE | 5 to 20% |
| DICAPRYLYL CARBONATE | 1 to 10% |
| DIBUTYL ADIPATE | 1 to 10% |
| GLYCEROL CAPRYLOCAPRATE | 1 to 10% |
| ETHYLHEXYL TRIAZONE | 1 to 10% |
| DIETHYLAMINO HYDROXYBENZOYL HEXYL BENZOATE | 1 to 10% |
| BIS-ETHYLHEXYLOXYPHENOL METHOXYPHENYL TRIAZINE | 1 to 10% |
| AVOCADO OIL | 1 to 5% |
| ALPHA-TOCOPHEROL | 0 to 1% |
| PURIFIED WATER | QS to 100 |
| GLYCEROL | 1 to 5% |
| XANTHAN GUM | 0 to 1% |
| POTASSIUM CETYL PHOSPHATE | 0 to 2% |
| ARGININE | 0 to 2% |
| PHENYLBENZIMIDAZOLE SULFONIC ACID | 1 to 5% |
| PRESERVING AGENTS | 0 to 2% |
| AVOCADO PERSEOSE | 0 to 1% |
| LAURYLGLUCOSE-GLYSTEARATE | 1 to 10% |

TABLE 2

| Sun protection milk | |
|---|---|
| Raw material/Trade name | % |
| MIGLYOLGELB | 1 to 10% |
| COPRA CAPRYLATE/CAPRATE | 5 to 20% |
| DICAPRYLYL CARBONATE | 1 to 10% |
| DIBUTYL ADIPATE | 1 to 10% |
| GLYCEROL CAPRYLOCAPRATE | 1 to 10% |
| ETHYLHEXYL TRIAZONE | 1 to 10% |
| DIETHYLAMINO HYDROXYBENZOYL HEXYL BENZOATE | 1 to 10% |
| BIS-ETHYLHEXYLOXYPHENOL METHOXYPHENYL TRIAZINE | 1 to 10% |
| TITANIUM DIOXIDE | 1 to 10% |
| AVOCADO OIL | 1 to 5% |
| ALPHA-TOCOPHEROL | 0 to 1% |
| PURIFIED WATER | QS to 100 |
| GLYCEROL | 1 to 5% |
| XANTHAN GUM | 0 to 1% |
| POTASSIUM CETYL PHOSPHATE | 0 to 2% |
| ARGININE | 0 to 2% |
| PHENYLBENZIMIDAZOLE SULFONIC ACID | 1 to 5% |
| PRESERVING AGENTS | 0 to 2% |

TABLE 2-continued

Sun protection milk

| Raw material/Trade name | % |
|---|---|
| AVOCADO PERSEOSE | 0 to 1% |
| LAURYLGLUCOSE-GLYSTEARATE | 1 to 10% |

TABLE 3

Sun protection cream

| Raw material/Trade name | % |
|---|---|
| PURIFIED WATER | QS to 100 |
| TITANIUM DIOXIDE | 1 to 25% |
| COPRA CAPRYLATE/CAPRATE | 1 to 10% |
| DICAPRYLYL CARBONATE | 1 to 10% |
| MIGLYOL GEL | 1 to 10% |
| GLYCEROL CAPRYLOCAPRATE | 1 to 10% |
| POLYGLY-2 DIPOLYHYDRO-STEARATE | 1 to 10% |
| POLYGLYCERYL-3 DIISOSTEARATE | 1 to 10% |
| AVOCADO OIL | 1 to 5% |
| GLYCEROL | 1 to 5% |
| PRESERVING AGENTS | 1 to 2% |
| MAGNESIUM SULFATE | 1 to 2% |
| ALPHA-TOCOPHEROL | 0 to 1% |
| XANTHAN GUM | 0 to 1% |
| ARGININE | 0 to 1% |
| AVOCADO PERSEOSE | 0 to 1% |

Similarly, as reference active ingredient, skilled persons can use any active ingredient known in the prior art for its effect in the prevention of harmful UV effects on the skin.

In particular, skilled persons can use avocado perseose that has previously been shown to prevent the harmful effects of UV rays (see application FR 1351136).

By avocado perseose it is referred herein to a C7 sugar or derivative thereof, or to a mixture of C7 sugars of following formula (I):

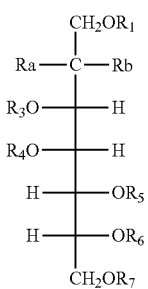

(I)

where:
Ra is a hydrogen atom and Rb is —OR$_2$, or CRaRb is the CO radical;
R$_1$, R$_2$, R$_3$, R$_4$, R$_5$, R$_6$ and R$_7$ are each independently:
a hydrogen atom, or
a —(CO)—R radical where R is a saturated or unsaturated hydrocarbon chain having 11 to 24 carbon atoms, optionally substituted by one or more substituents selected from the group consisting of hydroxy radicals (—OH), ethoxy radicals (—OC$_2$H$_5$) and —SO$_3$M group where M is a hydrogen atom, ammonium ion NH$_4^+$ or metal ion; or
a —(CO)—R' radical where R' is a saturated or unsaturated hydrocarbon chain having 2 to 10 carbon atoms, optionally substituted by one or more substituents selected from the group consisting of hydroxy radicals (—OH), ethoxy radicals (—OC$_2$H$_5$) and —SO$_3$M group with M representing a hydrogen atom, ammonium ion NH$_4^+$ or metal ion.

The reference active ingredient can also be selected from among active ingredients conventionally used in dermatology or cosmetics such as emollients, hydrating agents, skin barrier restructuring agents, PPAR agonists (Peroxysome Proliferator Activated Receptor), RXR or LXR agonists, healing agents, anti-irritant agents, soothing agents, anti-inflammatory agents, antioxidant agents, mineral or organic sunscreens or filters, antifungal compounds, antibacterial agents, preserving agents.

More particularly, the healing and/or skin barrier restructuring agents able to be used are advantageously panthenol (vitamin B5), arabinogalactan, zinc oxide, ceramides, cholesterol, squalane and phospholipids.

The anti-inflammatory and/or anti-irritant and/or soothing agent may be arabinogalactan or sunflower oleodistillate.

The sun protection active ingredients able to be used are advantageously UVB and/or UVA sunscreens and filters such as mineral and/or organic screens or filters known to skilled persons who can adapt the choice and concentration thereof as a function of the desired level of protection.

The preserving agents able to be used are those generally used for example in cosmetics, molecules having antibacterial action (pseudo-preserving agents) such as caprylic derivatives e.g. glycine capryloyl and glyceryl caprylate; hexanediol, sodium levulinate, and zinc and copper derivatives (gluconate and PCA).

The reference active ingredient may be selected in particular from among plant extracts, particularly:
vegetable oils such as soybean oil and/or rapeseed oil, avocado oil (WO2004/012496, WO2004/012752, WO2004/016106, WO2007/057439), lupin oil and advantageously sweet white lupin oil (WO98/47479), or a mixture of these oils;
oleodistillates or concentrates of vegetable or animal oils in particular sunflower, more advantageously linoleic concentrates of sunflower such as sunflower oil high in unsaponifiables (Soline®—WO2001/21150) marketed by Laboratoires Expanscience, unsaponifiable-concentrated oils of avocado, rapeseed or corn type useful in particular for their hydrating and/or emollient, healing and/or skin barrier restructuring, anti-inflammatory and/or anti-irritant and/or soothing action;
the unsaponifiables of plants or vegetable oil, advantageously avocado furans (Avocadofurane), able to be obtained using the method described in international application WO 01/21605, the unsaponifiables of avocado and/or soybean, more particularly a mixture of furanic avocado unsaponifiables and soybean unsaponifiables advantageously in a respective ratio of 1:3-2:3 (such as Piasclédine®), soybean unsaponifiables (such as obtained using the method described in international application WO 01/51596), sterol unsaponifiables (typically unsaponifiables having a sterol, methylsterol and triterpene alcohol content of between 20 and 95 weight %, preferably 45-65 weight % relative to the total weight of the unsaponifiable), phytosterols, sterol esters and vitamin derivatives useful in particular for their healing and/or skin barrier restructuring action and/or anti-inflammatory action;
the peptides or complexes of plant amino acids in particular of avocado (such as those described in international application WO2005/105123), the peptides of lupin (such as those described in international application WO 00/62789), total lupin extract (such as those described in international application WO2005/102259), the peptides of quinoa (such as those described in international application WO2008/080974), maca peptides (such as those described in international application WO2004/112742), soybean peptides fermented or unfermented, rice peptides (such as those described in international application WO2008/009709), useful in particular for their hydrating and/or emollient action (avocado), keratin-regulating action (lupin, quinoa), healing and/or skin barrier restructuring action (maca, quinoa, soybean), anti-inflammatory and/or anti-irritant and/or soothing action (lupin, quinoa), antioxidant action (avocado), schizandra peptides (such as those described in patent application FR 0955344), extract of *Acacia macrostachya* seeds (such as the extract described in patent application FR 0958525), extract of *Vigna unguiculate* seeds (such as the extract described in patent application FR 0958529); extract of *Passiflora* seeds such as the extract described in patent application FR 1262234);

Extracts high in polyphenols, and more particularly extracts of avocado fruit (such as those described in application FR 1 061 055), extracts of maca leaves (such as those described in application FR 1 061 047), and extracts of the above-ground parts of *Gynandropsis gynandra* (such as those described in application FR 1 061 051), Lupeol (FR 2 8 22 821, FR 2 857 596) useful in particular to promote healing;

Cupuacu butter, particularly appreciated for its hydrating properties;

The reference active ingredient may also be selected in particular from among oxazolines, in particular those selected from the group consisting of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline (preferably 2-undecyl-4,4-dimethyl-1,3-oxazoline called OX-100 or Cycloceramide®; WO 2004/050052, WO 2004/050079 and WO 2004/112741). They are particularly useful for their anti-inflammatory and/or anti-irritant and/or soothing action, antioxidant action.

Stem cell protecting or activating compounds such as Stemoxydine® (diethyl pyridine-2,4-dicarboxylate), Survicode™ (sodium cocoyl alaninate), Survixyl IS™ (pentapeptide-31), Defensil® (octyldodecanol, *Echium Plantagineum* Seed Oil, *Cardiospermum Halicacabum* Flower/Leaf/Vine Extract, *Helianthus Annuus* Sunflower Seed Oil Unsaponifiables), Celligent® (*Helianthus Annuus* Sunflower Seed Oil, Ethyl Ferulate, Polyglyceryl-5 Trioleate, *Rosmarinus Officinalis* Leaf Extract, Aqua, Disodium Uridine Phosphate), Phycosaccharide AI® (alginic acid, sodium salt, hydrolysed), Phycojuvenine® (*Laminaria digitata* extract), PhytoCellTec™ containing extracts of alpine white rose or Gamay Teinturier Freaux grape or Uttwiler spatlauber apple (*Malus domestica*) or argan stem cells, plant stem cells extracted from *Vitis vinifera* vines, plant stem cells of young Criste Marine shoots can also be reference active ingredients in the meaning of the invention.

According to another preferred embodiment, the reference expression level of a biomarker is the expression level of said marker obtained in a skin model comprising keratinocytes obtained from subjects aged three years or younger, preferably two years or younger, more preferably one year or younger, further preferably six months or younger and in particular aged three months or younger, not treated with the formulation or active ingredient of interest and not exposed to UV.

According to another embodiment, the reference expression level of a biomarker is the expression level of said marker obtained in a skin model comprising keratinocytes obtained from subjects aged three years or younger, preferably two years or younger, more preferably one year or younger, further preferably six months or younger and in particular aged three months or younger, treated with the formulation or active ingredient of interest and not exposed to UV.

Persons skilled in the art will also easily understand that the comparison at step d) is preferably performed between measurements of expression levels obtained with skin models comprising keratinocytes obtained from subjects aged three years or younger, preferably two years or younger, more preferably one year or younger, further preferably six months or younger and in particular aged three months or younger having similar even identical histological structures. By "similar histological structures" in the meaning of the present application is meant the relative proportions of the cell types included in the compared skin models are similar. For example it is preferable that the relative proportions of the cell types included in the skin model at step a) do not differ by more than 5% from the relative proportions of the cell types included in the skin model used to obtain a reference expression level at step d). By "relative proportion of cell type" in the meaning of the present application is meant the ratio of the number of cells corresponding to this cell type to the number of total cells included in the skin model. Therefore it is preferable for example that the proportion of keratinocytes in relation to the number of total cells in the skin model at step a) should not differ by more than 5% from the proportion of keratinocytes in relation to the total number of cells in the skin model used to obtain the reference expression level at step d). By "identical histological structures" in the meaning of the present application is meant that the relative proportions of cell types included in the compared skin models are identical. In the meaning of the invention the relative proportions of cell types included in the nipple skin model at step a) are identical to the relative proportions of the cell types included in the skin model used to obtain the reference expression level at step d) when they do not differ by more than 0.1%. Advantageously the proportion of keratinocytes relative to the total number of cells in the skin model at step a) does not differ by more than 0.1% from the proportion of keratinocytes in relation to total number of cells in the skin model used to obtain the reference expression level at step d).

Persons skilled in the art will understand just as easily that the comparison at step d) is preferably performed between measurements of expression levels obtained for skin models of similar even identical size, volume or weight. Therefore it is preferable that the size, volume or weight of the skin model at step a) do not differ by more than 5% from the size, volume or weight of the skin model used to obtain the reference expression level at step d). More preferably, the size, volume and weight of the skin model at step a) do not differ by more than 5% from the size, volume and weight of the skin model used to obtained the reference expression level at step c). Further preferably the size, volume and weight of the skin model at step a) do not differ by more than 0.1% from the size, volume and weight of the skin model used to obtain the reference expression level at step d).

Alternatively, if the skin models differ by more than 5% in size, volume and weight, it is within the reach of skilled persons to normalise the level obtained at step c) and the reference level of step d) using a normalisation factor.

This normalisation factor may be a directly accessible physical marker for example such as the cell mass of the sample or the mass of cell constituents such as the DNA cell mass or protein cell mass.

It may also be advantageous to use as normalisation factor the expression level of a gene which is expressed at the same level in all or nearly all the cells of the body. In other words, according to one particular embodiment of the present invention, as normalisation factor the expression level is used of a housekeeping gene. According to another embodiment, the level obtained at step c) and the reference level of step d) are normalised using the expression level not of the housekeeping genes but of the proteins they encode. A housekeeping gene is a gene expressed in all cell types which encodes a protein having a basic function necessary for survival of all cell types. A list of human housekeeping genes can be found in Eisenberg et al. (Trends in Genetics 19: 362-365, 2003). The housekeeping genes of the invention include for example the following genes: B2M, TFRC, YWHAZ, RPLO, 18S, GUSB, UBC, TBP, GAPDH, PPIA, POLR2A, ACTB, PGK1, HPRT1, IPO8 and HMBS.

Skilled persons are able to easily evaluate the efficacy of the formulation of interest as a function of the comparison at step d).

For example, when the expression level of PTGS2, IL1, IL8, IL1-R, IL1-RN, MMP1a or MMP3 measured at step c) is equal to or lower than the expression level of these markers obtained in a skin model not treated with the formulation of interest, then the formulation or active ingredient as the case may be is effective in preventing harmful UV effects on the skin of children aged three years or younger, preferably two years or younger, more preferably one year or younger, further preferably six months or younger and in particular aged three months or younger.

For example when the expression level of PTGS2, IL1, IL8, IL1-R, IL1-RN, MMP1a or MMP3 measured at step c) is equal to or is not higher by more than 10% than the expression level of these markers obtained in a skin model not exposed to UV, then the formulation is effective in preventing harmful UV effects on the skin of children aged three years or younger, preferably two years or younger, more preferably one year or younger, further preferably six months or younger and in particular aged three months or younger.

A further subject of the invention is a kit to implement a method of the invention comprising the necessary means for measuring the expression level of at least skin inflammation marker where the skin inflammation marker is preferably selected from the group consisting of PTGS2, interleukins preferably IL1α and IL8, the IL1 receptor: IL1-R, antagonist of the IL1 receptor: IL1-RN, matrix metalloproteases preferably MMP1 and MMP3.

According to one particular embodiment, the kit of the invention further comprises the means required to measure the expression level of at least one biomarker selected from the group consisting of:
  antioxidant defence, antimicrobial or DNA markers, said antioxidant defence or antimicrobial marker preferably being selected from the group consisting of catalase, superoxide dismutase 1, defensins in particular defensin β4, the p53 tumour suppressor protein; and
  markers of the epidermal barrier, said epidermal barrier marker preferably being selected from the group consisting of filaggrin, keratin 1, sciellin, loricrin, claudin 1, barx2; and
  markers of skin adhesion and repair, said skin adhesion and repair marker preferably being selected from among cell adhesion molecule 1, molecule CD36, fibronectin 1; and
  markers preferably expressed in stem cells, said marker preferably expressed in stem cells preferably being selected from among the p63 tumour suppressor protein, survivin.

Preferably the kit of the invention comprises the means required to measure the expression level of a combination of biomarkers comprising or consisting of:
  at least one skin inflammation marker where the skin inflammation marker is preferably selected from the group consisting of PTGS2, interleukins, preferably IL1α and IL8, the IL1 receptor: IL1-R, antagonist of the IL1 receptor: IL1-RN, matrix metalloproteases preferably MMP1 a and MMP3; and
  at least one antioxidant defence, antimicrobial or DNA marker, said antioxidant defence or antimicrobial marker preferably being selected from the group consisting of catalase, superoxide dismutase 1, defensins in particular defensin β4, the p53 tumour suppressor protein; and
  at least one marker of the epidermal barrier, said epidermal barrier marker preferably being selected from the group consisting of filaggrin, keratin 1, sciellin, loricrin, claudin 1, barx2; and
  at least one skin adhesion and repair marker, said skin adhesion and repair marker preferably being selected from among cell adhesion molecule 1, molecule CD36, fibronectin 1; and
  at least one marker preferably expressed in stem cells, said marker preferably expressed in stem cells preferably being selected from among the p63 tumour suppressor protein, survivin.

According to one particularly advantageous embodiment, the kit of the invention comprises the means required to measure the expression level of a combination of biomarkers comprising or consisting of PTGS2, IL1α, IL8, IL1-R, IL1-RN, MMP1, MMP3, catalase, superoxide dismutase 1, β4 defensin, p53 tumour suppressor protein, filaggrin, keratin 1, sciellin, loricrin, claudin 1, barx2, cell adhesion molecule 1, molecule CD36, fibronectin 1, p63 tumour suppressor protein and survivin.

Preferably the means required to measure the expression level of the markers PTGS2, IL1α, IL8, IL1-R, IL1-RN, MMP1, MMP3, catalase, superoxide dismutase 1, 34 defensin, p53 tumour suppressor protein, filaggrin, keratin 1, sciellin, loricrin, claudin 1, barx2, cell adhesion molecule 1, molecule CD36, fibronectin 1, p63 tumour suppressor protein and survivin comprise nucleic probes and/or amplification primers capable of binding to at least one of these biomarkers in nucleotide form.

The following examples are provided for illustration purposes and unless otherwise indicated are not intended to be limiting.

EXAMPLES

1. UV Effect on Infant and Child Epidermises
1.1. Introduction
  In this study the reconstructed epidermises were obtained with keratinocytes from a three-month old infant and child aged 11 years.
  In these two models the effect of UV radiation was evaluated by:
    RT-qPCR analysis of the expression of a selection of markers;

histological analysis of tissues and analysis of the formation of sunburn cells;

analysis by immunolabelling of the expression of integrin alpha 6.

1.2. Material and Methods

The epidermises were obtained with keratinocytes from the different donors in accordance with the model derived from the method of Poumay et at (Arch Dermatol Res 2004; 296: 203-11). After 2 days' culture in immersion the reconstructed epidermises were cultured at the air/liquid interface for 10 days. All experimental conditions were performed in duplicate, n=2.

For each epidermis batch, at D10 the epidermises were incubated for 24 h.

After incubation, the epidermises were irradiated with a dose of 500 mJ/cm$^2$ UVB+7255 mJ/cm$^2$ UVA. After irradiation, the epidermises were incubated for 30 min (integrin alpha 6 labelling) or 24 hours (analysis of gene expression and histology). Each age included a non-treated, non-irradiated batch and a non-treated, irradiated batch.

1.2.1. Histology

After incubation, the epidermises were rinsed and either frozen in liquid nitrogen isopentane and stored at −80° C. or fixed in formaldehyde. The fixed tissues were then dehydrated in ethanol baths and embedded in paraffin. Sections were prepared using a microtome (5 μm thick, several sections per slide, 1 slide per epidermis) and held at ambient temperature until staining.

The sections were deparaffined and stained following the conventional hematoxylin/eosin staining protocol. After rinsing, the sections were mounted between slides and coverslips.

The sections were observed under a NIKON E400 microscope. The digital images were recorded with a NIKON DS-Ri1 camera using NIS-Elements 3.10 software.

The sunburn cells were counted and compared with the total surface area of the reconstructed epidermises.

1.2.2. In Situ Immunolabelling

Sections were obtained from frozen epidermises using a cryostat (5 μm thick, several sections per slide, 1 slide per epidermis). The cryosections were fixed with an acetone/methanol mixture and dried in ambient air. After saturation in 5% PBS-T-milk, the sections were incubated at ambient temperature for 1 hour with the primary antibody directed against integrin alpha 6. After washing in PBS, labelling was detected with a secondary antibody directly coupled to an Alexa 488 fluorochrome. The cell nuclei were stained with propidium iodide solution. The sections were washed and mounted between slides and coverslips in an aqueous medium.

The sections were observed under a NIKON E400 microscope. The digital images were recorded using a NIKON DS-Ri1 camera and NIS-Elements 3.10 software. Fluorescence intensities were measured using ImageJ software.

1.2.3. Analysis of Differential Expression of the Genes

Expression of the markers was evaluated by RT-qPCR on the messenger RNAs extracted from the reconstructed epidermises of each treatment.

Analysis of gene expression was performed with n=2 using a PCR array (mQPA-STRESS-UV-64) containing 62 genes of interest and 2 reference genes (housekeeping genes).

The total RNAs of each sample were extracted with TriPure Isolation Reagent following the supplier's recommended protocol. RNA quantity and quality were evaluated by capillary electrophoresis (Ambion). Complementary DNAs (cDNA) were synthesized by reverse transcription of the RNAs in the presence of oligo(dT) and Superscript II enzyme. The cDNA obtained was quantified by spectrophotometry and the cDNA were adjusted to 10 ng/μl.

The PCR reactions were obtained using quantitative PCR with the "light cycler" system (Roche Molecular System Inc) and following the supplier's recommended protocol.

The reaction mixture for each sample was: cDNA 10 ng/μl, primers of the different markers used, reaction mixture containing the taq DNA polymerase enzyme, SYBR Green I marker (DNA intercalating agent) and MgCl$_2$.

Incorporation of fluorescence in amplified DNA was continuously measured throughout the PCR cycles. These measurements allowed fluorescence intensity curves to be obtained as a function of the PCR cycles and hence evaluation of a relative expression value for each marker. The number of cycles was determined from the "crossing" points of the fluorescence curves. For one same analysed marker, the more a sample is late "crossing" (high number of cycles) the lower the initial number of RNA copies.

The relative expression value is expressed in arbitrary units (AU) as per the following formula: $(1/2^{number\ of\ cycles}) \times 10^6$.

The expression of the genes of interest was normalised by the expressions of the 2 reference genes.

The expression percentages of the genes in the irradiated epidermises were then calculated in relation to their expression in non-irradiated epidermises (non-irradiated control) set at 100%. (Table 5).

TABLE 4

Classification of genes:

| Cluster name | Abbreviation | Gene name |
|---|---|---|
| Housekeeping | RPS28 | Ribosomal protein 28S |
| | GADPH | Glyceraldehyde-3-phosphate dehydrogenase |
| Inflammation | IL1A | Interleukin 1, alpha |
| | IL1RN | Interleukin 1 receptor antagonist |
| | IL8 | Interleukin 8 |
| | PTGS2 | Prostaglandin-endoperoxidase synthase 2 (prostaglandin G/H synthase and cyclooxygenase) |
| | MMP1 | Matrix metallopeptidase 1 |
| | MMP3 | Matrix metallopeptidase 1 |
| Antioxidant defence, antimicrobial, DNA protection, | CAT | Catalase |
| | SOD1 | Superoxide dismutase 1, soluble |
| | DEFB4 | Defensin, beta 4 |
| | TP53 | Tumor protein p53 |
| Epidermal differentiation, barrier function | FLG | Filaggrin |
| | KRT1 | Keratin 1 |
| | SCEL | Sciellin |
| | LOR | Loricrin |
| | CLDN1 | Claudin 1 |
| | BARX2 | BARX homeobox 2 |
| Cell-cell interaction, matrix adhesion and epidermal repair | CADM1 | Cell adhesion molecule 1 |
| | CD36 | CD36 molecule (thrombospondin receptor) |
| | FN1 | Fibronectin 1 |
| Stem cells | TP63 | Tumor protein p63 |
| | BIRC5 | Baculoviral IAP repeat-containing 5 or survivin |

1.3. Results 1.3.1. Histology

The reconstructed epidermises had expected morphology at D12. The different cell layers were present:
 basal layer
 spinous layer
 granular layer
 homey layer, anucleate.

As shown in FIG. 1, no histological difference was observed between the 3-month and 11-year epidermises. However UV radiation caused distinct deterioration of the 3-month epidermal horny layer which peeled off from the remainder of the epidermis, whereas the epidermis and horny layer remained practically unchanged after radiation in the 11-year epidermis. Histology of the 11-year reconstructed epidermises was comparable with that of reconstructed adult epidermises irradiated under the same conditions.

Sunburn cells were identified by their characteristic morphology (FIG. 1): dark basophilic nucleus, pycnotic and condensed, eosinophilic cytoplasm and formation of intercellular spaces.

Sunburn cells were present in large number in the irradiated epidermises with a higher number however in the irradiated 3-month epidermises.

The 3-month reconstructed epidermises therefore underwent stronger deterioration with UV radiation than the 11-year epidermises.

1.3.2. Gene Expression Profiles

As expected, UV irradiation of the reconstructed epidermises led to strong modulation of a good number of genes.

In particular the inflammation genes were overexpressed whilst the antioxidant defence, antimicrobial and DNA protection genes were repressed. In addition, the expression of epidermal differentiation and barrier function genes and of the genes involved in cell-cell interactions and in matrix adhesion having a role in epidermal repair was inhibited by UV radiation.

Finally, the expression of stem cell genes was highly inhibited 24 h after irradiation.

The 3-month reconstructed epidermises were more sensitive to UV radiation with a large number of genes showing modulation (inhibition or stimulation) much more clearly marked than in the irradiated 11-year epidermises (Table 5).

TABLE 5

% stimulation or repression of the genes of interest in the irradiated epidermises compared with non-irradiated epidermises.

| Genes | 3 months | 11 years |
|---|---|---|
| | % stimulation | |
| IL1A | 2897 | 1679 |
| IL1RN | 813 | 476 |
| IL8 | 1660 | 1112 |
| PTGS2 | 2361 | 307 |
| MMP1 | 2141 | 390 |
| MMP3 | 4565 | 261 |
| | % repression | |
| CAT | 66 | 52 |
| SOD1 | 65 | 52 |
| DEFB4 | 94 | 75 |
| TP53 | 73 | 42 |
| FLG | 75 | 59 |
| KRT1 | 71 | 29 |
| LOR | 67 | 21 |
| SCEL | 54 | 0 |
| CLDN1 | 35 | 17 |
| BARX2 | 79 | 15 |
| CADM1 | 58 | 41 |
| CD36 | 59 | 50 |
| FN1 | 73 | 0 |
| TP63 | 69 | 56 |
| BIRC5/SURVIVIN | 73 | 56 |

The inflammation genes exhibited greater overexpression in the irradiated 3-month epidermises FIG. 2), showing greater reactivity to the sun.

The defence genes exhibited greater repression in the irradiated 3-month epidermises (FIG. 3) showing a lower capacity of defence. The damage caused by UV is less easily repaired.

The barrier genes showed greater repression in irradiated 3-month epidermises (FIG. 4), indicating lesser protection against the environment. The damage caused by UV is less easily repaired.

The epidermal repair genes showed greater repression in irradiated 3-month epidermises (FIG. 5), showing lesser capacity to repair and heal skin after UV exposure.

The genes of epidermal stem cells showed greater repression in irradiated 3-month epidermises (Figure -) indicating lesser capacity to regenerate the skin and maintain proper equilibrium.

1.4. Immunolabelling of Integrin Alpha 6

FIG. 7 and Table 6 show that the expression of integrin alpha 6 (periplasmic labelling) is identical in the epidermises of both age groups, but UV radiation considerable reduces integrin alpha 6 in the 3-month epidermises;

TABLE 6

% repression of integrin alpha 6 protein in irradiated epidermises compared with non-irradiated epidermises.

| | 3 months | 11 years |
|---|---|---|
| Integrin alpha 6 | 48% | 25% |

All these results clearly show that reconstructed 3-month and 11-year epidermises do not react in similar manner to UV radiation. The harmful effects of UV rays are higher in 3-month epidermises showing the greater sensitivity to sun of the skin of infants and young children through greater reactivity and less capability to protect and repair damage.

2. Evaluation of the Photoprotective Potential of Sun Cream Containing Avocado Perseose 2.1. Material and Methods The epidermises were obtained from keratinocytes isolated from a 3-month old donor following the previously described protocol. For each epidermis batch at D10 the epidermises were incubated for 24 h. After incubation, the epidermises were treated with a sun cream then irradiated with a dose of 500 mJ/cm$^2$ UVB+7255 mJ/cm$^2$ UVA. After irradiation, the epidermises were incubated for 24 hours. The batches therefore included one non-treated and non-irradiated batch, one non-treated, irradiated batch and one batch treated with sun cream and irradiated. All experimental conditions were performed in duplicate, n=2.

Histological analysis also allowing counting of sunburn cells and analysis of differential gene expression were conducted as previously described.

2.2. Results

As shown in FIG. 8 the harmful effects observed after irradiation of 3-month epidermises were no longer found when the sun cream was topically applied to these 3-month epidermises. This protective effect of the sun cream on the epidermal structure was also demonstrated with the disappearance of the sunburn cells the formation of which had been induced by radiation.

The sun cream distinctly protected reconstructed 3-month epidermises against UV-induced damage.

Similarly, the expression levels of the genes strongly modulated by UV irradiation were regulated after application of the sun cream.

The sun cream applied to irradiated 3-month epidermises strongly reduced the expression of inflammation genes and increased the expression level of defence genes, epidermal function genes and stem cell genes (Table 7).

This confirms the efficacy of this cream in protecting the skin of infants and children against sun exposure.

TABLE 7

Expression level of inflammation, defence, barrier function and stem cell genes modulated by UV in 3-month epidermises with or without a sun product.

| Genes of interest | | Relative expression in irradiated 3-month epidermis compared with non-irradiated 3-month epidermis | Relative expression in irradiated 3-month epidermis with sun product compared with irradiated 3-month epidermis without |
|---|---|---|---|
| Inflammation | MMP1 | 2241 | 4 |
| | PTGS2 | 2461 | 4 |
| Defence | CAT | 34 | 112 |
| | P53 | 27 | 157 |
| Barrier function | LOR | 33 | 205 |
| | BARX2 | 21 | 110 |
| Stem cells | TP63 | 33 | 108 |

The invention claimed is:

1. A method, comprising the following steps:
   a. contacting a formulation or a compound with a skin model comprising keratinocytes obtained from subjects aged three years or younger;
   b. exposing the contacted skin model of step a) to UV;
   c. measuring the transcript or protein expression level of a combination of biomarkers comprising or consisting of:
   at least one skin inflammation marker selected from the group consisting of Prostaglandin G/H Synthase 2 (PTGS2), Interleukin 1α (IL1α), Interleukin 8 (IL8), Interleukin 1 (IL1) receptor (IL1-R), IL1 receptor antagonist (IL1-RN), Matrix Metallopeptidase 1, and Matrix Metallopeptidase 3; and
   at least one DNA marker selected from the group consisting of catalase, superoxide dismutase 1, defensins, and tumor protein p53 (p53); and
   at least one epidermal barrier marker selected from the group consisting of filaggrin, keratin 1, sciellin, loricrin, claudin 1 and homeobox protein BarH-like 2 (barx2); and
   at least one skin adhesion and repair marker selected from among cell adhesion molecule 1 (CADM1), and platelet glycoprotein 4 (molecule CD36); and
   at least one marker expressed in stem cells selected from among tumor protein p63 (p63) and survivin, in the skin model of step b).

2. The method according to claim 1, wherein step c) comprises measurement of the transcript or protein expression level of a combination of biomarkers comprising or consisting of PTGS2, Interleukin 1α (IL1α), Interleukin 8 (IL8), IL1-R, IL1-RN, Matrix metalloproteinase-1 (MMP1), Matrix metalloproteinase-3 (MMP3), catalase, superoxide dismutase 1, defensin β4, p53, filaggrin, keratin 1, sciellin, loricrin, claudin 1, barx2, CADM1, molecule CD36, fibronectin 1, p63 and survivin.

3. The method of claim 1, wherein said interleukin is IL1α.

4. The method of claim 1, wherein said interleukin is IL8.

5. The method of claim 1, wherein said matrix metalloproteases is MMP1.

6. The method of claim 1, wherein said matrix metalloproteases is MMP3.

7. The method of claim 1, wherein said defensin is defensin β4.

8. The method of claim 1, wherein said children are aged two years or younger.

9. The method of claim 1, wherein said children are aged one year or younger.

10. The method of claim 1, wherein said children are aged six months or younger.

11. The method of claim 1, wherein said children are aged three months or younger.

* * * * *